(12) United States Patent
Pendyala et al.

(10) Patent No.: US 10,457,909 B2
(45) Date of Patent: Oct. 29, 2019

(54) HIGH YIELD ALGAL BIOMASS PRODUCTION WITHOUT CONCENTRATED CO₂ SUPPLY UNDER OPEN POND CONDITIONS

(71) Applicant: The University of Toledo, Toledo, OH (US)

(72) Inventors: Brahmaiah Pendyala, Toledo, OH (US); Agasteswar Vadlamani, Toledo, OH (US); Sridhar Viamajala, Toledo, OH (US); Sasidhar Varanasi, Toledo, OH (US); Mohammadmatin Hanifzadeh, Toledo, OH (US)

(73) Assignee: The University of Toledo, Toledo, OH (US)

( * ) Notice: Subject to any disclaimer, the term of this patent is extended or adjusted under 35 U.S.C. 154(b) by 127 days.

(21) Appl. No.: 15/498,621

(22) Filed: Apr. 27, 2017

(65) Prior Publication Data
US 2017/0313972 A1 Nov. 2, 2017

Related U.S. Application Data

(60) Provisional application No. 62/328,296, filed on Apr. 27, 2016.

(51) Int. Cl.
*C12N 1/12* (2006.01)
*C12M 1/00* (2006.01)
*C10L 1/02* (2006.01)

(52) U.S. Cl.
CPC ............... *C12N 1/12* (2013.01); *C10L 1/02* (2013.01); *C12M 21/02* (2013.01); *C12M 23/18* (2013.01); *C10L 2200/0469* (2013.01); *C10L 2290/06* (2013.01); *C10L 2290/26* (2013.01)

(58) Field of Classification Search
CPC . C12N 1/12; C12N 11/04; C12N 1/04; C12N 13/00; C12N 1/14; C12N 1/20; C12N 15/52; C12N 15/74; C12N 1/16; C12N 9/16; C12N 9/93; C12N 27/24111; C12N 15/8273; C12N 1/36; C12N 15/79; C12N 15/8243; C12N 15/8271; C12N 15/8274; C12N 15/8275; C12N 9/0067; A01G 33/00; A01G 29/00; C02F 3/32; C02F 3/02; C02F 2200/0469; C02F 2103/08; C02F 1/043; C02F 1/14; C02F 1/447; C02F 1/20; C02F 1/52; C02F 1/66; C02F 2103/007; C02F 3/005; C02F 3/322; C10L 5/40; C10L 5/44; C10L 1/02; C10L 2200/469; C10L 2290/04; C10L 2290/06; C10L 2290/26; C10L 2270/02; C10L 2270/04; C11D 3/2075; C11D 3/2096; C12M 21/02; C12M 23/18; C12M 27/00; C12M 25/02; C12M 29/04; C12M 43/04; C12M 43/08; C12M 29/02; C12M 29/18; C12M 29/20; C12M 23/34; C12M 29/08; C12M 47/02; C12M 23/40; C12M 25/00; C12M 29/24; C12M 41/44; C12M 41/46; C12M 41/48; Y02A 40/88; Y02A 50/2358; Y02A 20/212; Y02A 50/235; Y02W 10/37; Y02W 30/74; Y02W 30/47; A23K 10/30; A23L 17/60; A23L 33/105; Y02C 10/02; Y02E 50/10; Y02E 50/30; Y02E 50/13; Y02E 50/343; Y02E 10/52; Y02E 10/725; Y02E 2300/1014; Y02E 50/17; Y02E 60/366; Y02E 10/28; Y02E 60/527; Y02P 60/877; Y02P 20/52; Y02P 30/20; Y02P 20/152; Y02P 20/59; Y02P 20/133; Y02P 70/527; C12P 39/00; C12P 7/6463; C12P 7/649; C12P 5/00; C12P 7/64; C12P 7/6409; C12P 19/04; C12P 23/00; C12P 7/6427; C12P 3/00;
(Continued)

(56) References Cited

U.S. PATENT DOCUMENTS 3,521,400 A * 7/1970 Ort .................. A01G 33/00
47/1.4
8,192,628 B2 * 6/2012 Cranford .............. C11B 1/02
210/639
(Continued)

FOREIGN PATENT DOCUMENTS

CN        1563344 A  *  1/2005  ............... C12N 1/12

OTHER PUBLICATIONS

Vadlamani et al, "Enhanced Biomass and Lipid Productivities of Outdoor Alkaliphilic Microalgae Cultures through Increased Media Alkalinity", Dissertation Abstracts Int'l, vol. 79, No. 7B(E), Dec. 2016.*
(Continued)

*Primary Examiner* — Deborah K Ware
(74) *Attorney, Agent, or Firm* — MacMillan, Sobanski & Todd, LLC

(57) ABSTRACT

Methods and systems for efficient culturing of algae in open ponds. Further, the methods include a method for culturing algae in an open pond medium that is free of any concentrated supply of $CO_2$, and no concentrated source of $CO_2$ is used to supply carbon for culturing the algae. Also, the algae are cultured in the open pond which has a pH above 9.5. In addition, the open pond medium has incorporated therein an inorganic carbon buffer at a specified concentration under conditions for obtaining an increased biomass. Also, the pH above 9.5 permits sufficient increased fixation of atmospheric CO2 into the open pond medium.

19 Claims, 41 Drawing Sheets
(39 of 41 Drawing Sheet(s) Filed in Color)

(58) Field of Classification Search
CPC .. C12P 1/04; C12P 5/023; C12P 7/065; C12P 7/08; C12P 7/16; C12P 7/40; C12P 7/54; C12P 7/625; G01N 23/2257; G01N 33/82; C10G 2300/1014; C10G 3/00; C10G 3/50; C10G 47/00; C12Y 203/01039; C12Y 301/02; C12Y 602/01003; C12Y 604/01002; C12Y 112/07002; C09K 8/582; C09K 8/60; C09K 8/21; C09K 843/16; H02S 20/30; H02S 40/22; H02S 40/425; H02S 40/44; A01C 23/025; A01N 27/00; C01B 13/00; C01B 2203/84; C01B 3/34; C01B 3/48; B01D 1/0035; B01D 2251/95; B01D 2257/504; B01D 33/66; B01D 3/007; B01D 53/60; B01D 53/84; B01D 5/0006; B01D 5/0066; B01D 5/009; B01D 61/364; B01D 19/0036; B01D 19/0068; C05F 11/00; C12R 1/01; E21B 43/16; F03D 7/25; H02K 7/1807; C07K 14/405; C07K 14/00; C07K 14/43504; A61K 38/00; A61K 38/16; A01H 13/00; A01H 1/00; A01H 1/06; C25B 15/02; C25B 1/04; C11B 1/025; C11B 1/08; C11B 1/10; F03B 17/06; H01M 8/16; C12Q 1/26

See application file for complete search history.

(56) References Cited

U.S. PATENT DOCUMENTS

| | | | | |
|---|---|---|---|---|
| 9,718,702 | B2* | 8/2017 | Harper, Jr. | C02F 1/20 |
| 2011/0143012 | A1* | 6/2011 | Rettenmaier | B01D 53/84 426/648 |
| 2012/0282651 | A1* | 11/2012 | Yuan | C12P 39/00 435/42 |
| 2013/0305599 | A1* | 11/2013 | Rettenmaier | B01D 53/84 44/603 |
| 2013/0319059 | A1* | 12/2013 | Chen | B01D 53/60 71/23 |
| 2014/0242676 | A1* | 8/2014 | Abdel-Fattah | C12N 1/12 435/257.1 |
| 2018/0209925 | A1* | 7/2018 | Antici | G01N 23/2257 |

OTHER PUBLICATIONS

Science Alert, Soundarapandian et al, "Effects of Chemical Parameters on Spirulina platensis Biomass Production: Optimized M . . . " pages 1-18, Int. J. of Zoological Res. vol. 4 (1): 1-11, 2008.*

Bill Argo, "Understanding Plant Nutrition . . . Fertilizers and Macronutrients" , pp. 1-9, Jul. 2008.*

Chi et al., "Bicarbonate produced from carbon capture for algae culture", Trends in Biotechnology, 2011, vol. 29, No. 11, pp. 537-541.

* cited by examiner

HIGH YIELD ALGAL BIOMASS PRODUCTION WITHOUT CONCENTRATED $CO_2$ SUPPLY UNDER OPEN POND CONDITIONS

RELATED APPLICATIONS

This application claims priority to U.S. Provisional Application No. 62/328,296, filed under 35 U.S.C. § 111(b) on Apr. 27, 2016, the disclosure of which is incorporated herein by reference in its entirety for all purposes.

STATEMENT REGARDING FEDERALLY SPONSORED RESEARCH

This invention was made with government support under Grant Number CHE-1230609 awarded by the National Science Foundation, and Grant Number DE-EE0005993 awarded by the United States Department of Energy. The government has certain rights in this invention.

BACKGROUND OF THE INVENTION

Renewable energy from biomass (bioenergy) can mitigate anthropogenic $CO_2$ emissions due to reduced use of fossil energy. Cultivation of microalgae for bioenergy could be a superior and sustainable alternative to terrestrial energy crops, due to the fast growth rates of microalgae as well as their ability to grow on waste waters and marginal lands. While the potential of microalgae has been well-appreciated, present methods of cultivation pose significant hurdles in the way of economical production. Two methods of cultivation are closed photo-bio reactors and open-pond systems. Of these, open-pond systems are robust for large-scale algal cultivation.

Microalgae cultivation in open ponds is usually attempted in an autotrophic mode (i.e., photosynthetic carbon fixation) using mesophiles (viz., algae that grow in a near neutral pH environment). To achieve high photosynthesis rates, availability of dissolved inorganic carbon (DIC) (i.e., dissolved $CO_2$ and $HCO_3^-$) is generally crucial apart from light. Unfortunately, under mesophilic conditions, slow kinetics of atmospheric $CO_2$ absorption lead to limited DIC availability for biomass growth. Consequently, to increase the DIC, different approaches have been attempted. One of these approaches involves sparging raw flue gas or more concentrated $CO_2$ into the ponds. Providing concentrated $CO_2$ (either as flue gas or more concentrated $CO_2$) further for algae culture proves to be expensive, due to the high costs of $CO_2$ capture at the emission source using absorbents, regeneration of the absorbents, $CO_2$ transportation to algal ponds, the costs associated with its temporary storage, and incomplete uptake by the open pond culture medium.

Some alternatives to this approach involve contacting the sorbent solution containing the absorbed $CO_2$ with the open pond culture medium directly to strip the DIC into the culture, thus achieving cost reductions through elimination of sorbent regeneration and $CO_2$ storage steps. However, a drawback to these approaches is that they are constrained by (i) proximate availability of flue gas or other high concentration $CO_2$ sources, and (ii) the energy and infrastructure burden to deliver $CO_2$ over long distances, as well as its distribution into the pond-medium. It has been estimated that microalgae cultivation systems that are constrained by the availability of flue gases (in addition to low-slope barren lands and favorable climates) could achieve less than 10% of the Department of Energy's 2030 advanced fuel targets. In addition, it is believed that nearly 65% of cultivation-related variable operating costs are associated with recovery of $CO_2$ from flue gas and delivery to ponds (of a total operating cost of $144 per ton of dry algae, approximately $91 are attributable to $CO_2$ delivery to ponds). In terms of overall costs of cultivation (excluding harvesting costs, but including costs to service capital for pond construction), $CO_2$ supply contributes nearly $100 to the minimum biomass selling price (MBSP) of $400/ton of dry algae.

When "high-value" algae-based end-products are targeted (instead of fuel), an alternate strategy that could be justified is mixotrophic cultivation (i.e., supplementing $CO_2$-derived inorganic carbon with organic carbon such as glucose) to improve the biomass yield. However, in open pond cultivation systems, mixotrophic mode cultivation raises additional issues. For example, at the pH conditions conducive for mesophilic algal growth, simultaneous growth of predatory micro-organisms is also supported by the organic carbon source, leading to algae "culture-crash". Thus, there is a need for new and improved methods and systems for the culturing of algae.

SUMMARY OF THE INVENTION

Provided is a method for cultivation of algae without requiring concentrated $CO_2$ inputs. The cultures are grown at high pH (>9.5), which allows rapid absorption of atmospheric $CO_2$ and permits high growth rates (>10 $g/m^2/d$).

In one aspect, provided is a method for culturing algae, the method comprising culturing alkaliphilic algae in an open pond medium having a pH above 9.5, and incorporating into the open pond medium an inorganic carbon buffer sufficient to allow increased fixation of atmospheric $CO_2$ into the open pond medium, where the open pond medium is free from any concentrated supply of $CO_2$, and no concentrated source of $CO_2$ is used to supply carbon to the open pond medium. In certain embodiments, the inorganic carbon buffer comprises either a $NaHCO_3/Na_2CO_3$ mixture or a $KHCO_3/K_2CO_3$ mixture. In particular embodiments, the $NaHCO_3/Na_2CO_3$ mixture or $KHCO_3/K_2CO_3$ mixture is incorporated at a concentration ranging from about 7 mM to about 1 M. In certain embodiments, the pH is at least about 9.9. In certain embodiments, the method further comprises incorporating glucose or other sugars or carboxylic acids into the open pond medium. In certain embodiments, the algae achieve growth rates higher than 10 $g/m^2/d$. In certain embodiments, the algae comprise a *Chlorella* sp., *Dunaliella* sp., *Synechocystic* sp., *Cyanothece* sp., *Microcoleus* sp., *Euhalothece* sp., or *Spirulina* sp. strain.

In certain embodiments, the method further comprises incorporating Ca and/or Mg into the open pond at a concentration of less than 7 mg/L. In certain embodiments, the low Ca and Mg lead to production of biomass with higher carbohydrate and lipid content. In particular embodiments, the Ca is incorporated into the open pond at a concentration of less than 1.5 mg Ca/L. In particular embodiments, the Mg is incorporated into the open pond at a concentration of less than 0.5 mg Mg/L.

In certain embodiments, the method further comprises circulating the algae within the open pond medium. In certain embodiments, the method further comprises harvesting biomass from the cultured algae and recovering remnant media. In particular embodiments, the remnant media is recycled in a second open pond medium. In particular embodiments, the method further comprises converting the harvested biomass to one or more fuels. In particular embodiments, the converting comprises hydrothermal liquefaction to produce biocrude. In particular embodiments, the biocrude has a N content of less than 4%.

In certain embodiments, the method further comprises regulating nitrogen input in the open pond medium, in a range from about 5 mg/L to about 27 mg/L, so as to modulate the biochemical composition of the microalgae.

In certain embodiments, the open pond medium has a salinity in the range of from about 10 g/L to about 30 g/L, a pH greater than 10.0, and an alkalinity of up to about 1 M.

In certain embodiments, the method further comprises improving phycocyanin production by increasing one or more of biomass concentration, nitrogen concentration, and salinity in the open pond medium.

In another aspect, provided herein is an open pond system comprising a medium having a pH above 9.5 and exposed to solar radiation, an inorganic carbon buffer in the medium, and alkaliphilic algae in the medium, where the open pond system is free from any unnatural or concentrated $CO_2$ supply. In certain embodiments, the pH is at least about 9.9.

In certain embodiments, the open pond system further comprises an organic substrate in the medium. In particular embodiments, the organic medium comprises glucose or other sugars or carboxylic acids. In certain embodiments, the inorganic carbon buffer comprises either a $NaHCO_3$/$Na_2CO_3$ mixture or a $KHCO_3$/$K_2CO_3$ mixture. In particular embodiments, the $NaHCO_3$/$Na_2CO_3$ mixture or $KHCO_3$/$K_2CO_3$ mixture is incorporated at a concentration ranging from about 7 mM to about 1 M.

In certain embodiments, the algae comprises a *Chlorella* sp., *Dunaliella* sp., *Synechocystic* sp., *Cyanothece* sp., *Microcoleus* sp., *Euhalothece* sp., or *Spirulina* sp. strain. In certain embodiments, the open pond system further comprises a water-moving device configured to circulate the medium within the open pond system.

In certain embodiments, the medium further comprises Ca and/or Mg at a concentration of less than 7 mg/L.

In certain embodiments, the medium further comprises one or more nutrients selected from the group consisting of: $NaNO_3$, $MgSO_4$, $CaCl_2$, NaCl, ferric ammonium citrate, $H_3BO_3$, $MnCl_2$, $ZnCl_2$, $CuCl_2$, $Na_2MoO_4$, $CoCl_2$, $NiCl_2$, $V_2O_5$, and KBr.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 3A: Cell dry weight. FIG. 3B: Biomass productivity. FIG. 3C: Rapid light curve showing measurement of changes in electron transfer rate (ETR) with increasing incident photon intensity.

FIG. 5A: Cell dry weight. FIG. 5B: Biomass productivity. FIG. 5C: Rapid light curve.

FIG. 14A shows biomass productivity. FIG. 14B shows biomass produced/chlorophyll (g/g). FIG. 14C shows chlorophyll concentration. FIG. 14D shows nitrogen content in biomass (%). FIG. 14E shows maximum quantum yield ($F_V/F_M$). FIG. 14F shows FAME content.

FIG. 15A shows the results from batch 1, and FIG. 15B shows the results from batch 2.

DETAILED DESCRIPTION OF THE INVENTION

Figure 1A:
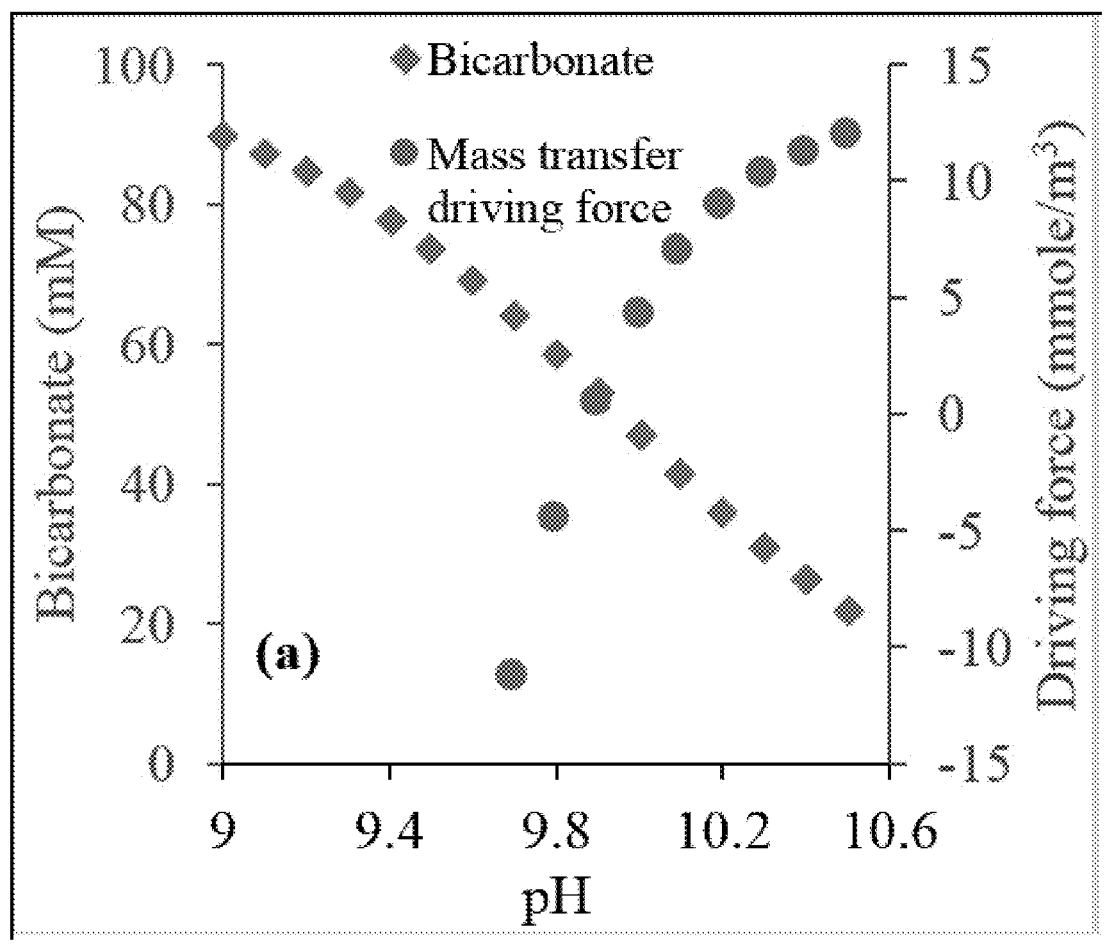
FIGS. 1A-1B: Graphs showing pH-dependent changes in bicarbonate concentrations and mass transfer driving force (FIG. 1A), and in enhancement factor and $CO_2$ flux (FIG. 1B).

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Provided is a method that can cultivate microalgae under high pH and alkalinity conditions at high productivity without a supply of concentrated $CO_2$ in any form. Consequently, the method reduces production costs up to 25%. Furthermore, the method allows for open ponds to be used in geographic areas not co-located with a source of $CO_2$. In other words, the method herein alleviates the need for an open pond to be in proximity to a flue gas source. In order to be able to achieve high growth rates using atmospheric $CO_2$ alone, media design is key. In general, the media should have a high pH to drive atmospheric $CO_2$ into solution at high rates, and should have a sufficient inorganic carbon "buffer" to allow rapid rates of $CO_2$ fixation. The algae strain must also be capable of withstanding both the high pH and high inorganic carbon concentrations in the media. The high pH conditions allow the use of organic carbon (e.g., glucose or other sugars or carboxylic acids) to be used as a substrate in low-cost open ponds, without concern of a culture crash because most bacteria do not survive in the high pH conditions of the medium. Further, the method produces lower amounts of nitrogen in the algae, which is advantageous for biofuel production from the harvested biomass.

In accordance with the present disclosure, the cultivation of alkaliphilic algae under appropriately tailored media conditions can eliminate most of the obstacles encountered with mesophilic algae cultivation in open-ponds. These include (1) the need to situate open ponds close to a $CO_2$ emission source, (2) costs associated with $CO_2$ concentration, and (3) the energy and infrastructure costs associated with the supply of $CO_2$ for commodity-scale biomass production. It is demonstrated herein that the high pH media conditions of alkaliphilic algae make it possible to carry out open-pond cultivation in "mixotrophic mode" without culture crash and without detrimental microbial contamination. These advantages are derived from the ability of highly alkaline solutions to efficiently absorb atmospheric $CO_2$, and the inability of predatory microorganisms to survive under alkaline conditions. Moreover, with this method, after harvesting the microalgae, the aqueous medium which has high inorganic carbon and other nutrients can be recycled indefinitely without compromising the algal growth. In addition, the cultivation conditions reduce the nitrogen content of the biomass—an aspect that is highly advantageous for producing low nitrogen content biofuels from biomass intermediates (such as through hydrothermal liquefaction). Furthermore, cultivation of alkaliphilic microalgae under high salinity environment promotes the production of phycocyanin, a high value pigment.

Alkaliphiles are organisms that thrive at high pH values (>9.5). As such, the cultivation medium is at an initial pH ~10 or higher, and contains high concentrations of inorganic carbon, up to 60-100 mM in the form of added $NaHCO_3$/$Na_2CO_3$ and/or $KHCO_3$/$K_2CO_3$. Alkaline solutions are especially effective in absorbing "atmospheric $CO_2$" and sustaining the productivity of algae, without the need for a concentrated $CO_2$ source and the infrastructure for $CO_2$ distribution. Simultaneously, the liquid phase equilibrium between $OH^-$, $CO_3^{2-}$, and $HCO_3^-$ allows the solution to contain high concentrations of $HCO_3^-$, which is a DIC form usable by microalgae through carbonic anhydrases.

The mass transfer flux of $CO_2$ ($J_{CO_2}$) from the atmosphere into highly alkaline bulk media is determined by (i) the driving force established by the concentration gradient of $CO_2$ between the gas-liquid interface ($[CO_{2(aq)}^*]$) and the bulk liquid ($[CO_{2(aq)}^{bulk}]$), (ii) an "enhancement factor" (E) that accounts for the enhancement of mass transfer rates due to reaction between (the acidic) $CO_2$ and the high concentration of hydroxyl ions in the mass transfer boundary layer, and (iii) the mass transfer coefficient ($k_L$):

$$J_{CO_2} = k_L \cdot E \cdot ([CO_{2(aq)}^*] - [CO_{2(aq)}^{bulk}]) \quad (1)$$

where $k_L$ is the physical mass transfer coefficient (m/h).

At the interface with air, the liquid-phase concentration of $CO_2$ ($[CO_{2(aq)}^*]$) is determined by the concentration of $CO_2$ in air (assumed to be 387 ppm) and the Henry's constant for $CO_2$ ($[CO_{2(aq)}^*]=0.013$ mM). In the bulk, the aqueous $CO_2$ concentration ($[CO_{2(aq)}^{bulk}]$) is determined by the simultaneous equilibria established among reactions shown in Equations 2, 3, and 4 coupled to the electro-neutrality (total alkalinity) requirement shown in Equation 5:

with $$K_1 = \frac{k_{11}}{k_{12}} = \frac{[HCO_3^-]}{[CO_{2(aq)}^{bulk}][OH^-]} = 4.5 \times 10^7 \frac{L}{mol} \text{ at } 25° \text{ C.}$$

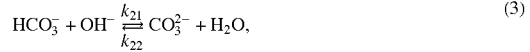

with, $$K_2 = \frac{k_{21}}{k_{22}} = \frac{[CO_3^{2-}]}{[HCO_3^-][OH^-]} = 4.9 \times 10^3 \frac{L}{mol} \text{ at } 25° \text{ C.}$$

with $$K_w = \frac{k_{31}}{k_{32}} = [H^+][OH^-] = 0.92 \times 10^{-14} \frac{mol^2}{L^2} \text{ at } 25° \text{ C.}$$

$$TA = [HCO_3^-] + 2[CO_3^{2-}] + [OH^-] \quad (5)$$

where TA is the "total alkalinity" of the system, and can be measured independently via titration. The equilibrium constant (K) values are from the literature. The plots in FIG. 1A (estimated by solving Equations 2-5) show that in a high alkalinity medium and at pH 10.2, approximately 35 mM $HCO_3^-$ is present along with a high $CO_2$ mass transfer driving force.

Figure 1B:
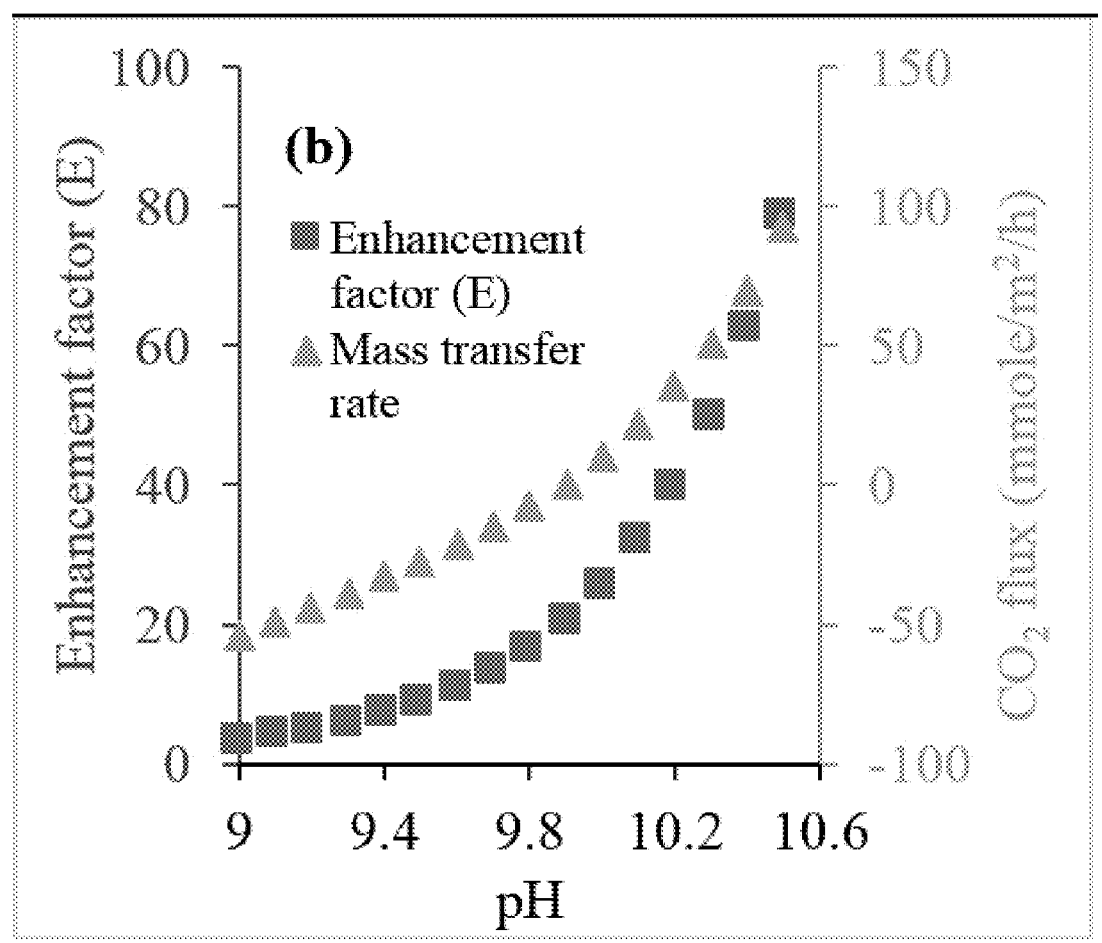

The pH driven enhancement factor (E) can significantly increase mass transfer rates in high pH media. For high alkalinity solutions reacting with small concentrations of $CO_2$, the concentrations of $CO_3^{2-}$ and $HCO_3^-$ can be considered essentially invariant in the mass transfer boundary layer. At these conditions, the enhancement factor can be estimated from the solution of the ordinary differential equations that describe the one-dimensional mass transport of $CO_2$ via the reaction shown in Eq. 2. The expression for E can be given as:

$$E = 1 + \frac{\mathcal{D}_{OH^-} \cdot \mathcal{D}_{HCO_3^-} \cdot K_1 \cdot [OH^-]}{\mathcal{D}_{CO_2}(K_1 \cdot CO_{2(aq)}^* \cdot \mathcal{D}_{HCO_3^-} + \mathcal{D}_{OH^-})} \quad (6)$$

where, the subscripted $\mathcal{D}$'s represent diffusion coefficients of the various dissolved species. As seen from Eq (6), at a constant temperature, is unction of solution pH only (see computed values in FIG. 1B; E at pH 10.2=40).

The physical mass transfer coefficient of $CO_2$ ($k_L$) in open raceway ponds has been previously estimated to be 0.1 m/h. At this $k_L$, the $CO_2$ mass transfer flux values can be estimated as a function of pH using computed values of E and ($[CO_{2(aq)}^*] - [CO_{2(aq)}^{bulk}]$) and shown in FIG. 1B. At pH 10.2, the mass transfer flux is approximately 35 mmole/m²/h, which corresponds to biomass productivity of 20 g/m²/d (assuming a biomass C-content of ~50%).

During cultivation, $HCO_3^-$ is taken up, $CO_2$ is abstracted and fixed, resulting in a net release of $OH^-$ as shown in Eqs. 7 and 8 below:

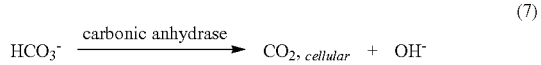

(7)

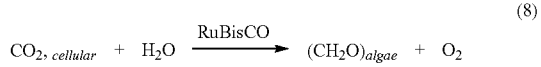

(8)

The production of OH⁻ shifts the DIC equilibrium towards $CO_3^{2-}$ (see Eq. 3) which, in turn, increases the driving force for $CO_2$ dissolution. Any net increase in pH and associated decrease of $HCO_3^-$ due to conversion to $CO_3^{2-}$ can be rebalanced at night, when photosynthesis is absent (Eq. 1).

Suitable alkaliphilic algae include, but are not limited to, eukaryotic microalgae such as *Chlorella* sp. and *Dunaliella* sp., as well as cyanobacteria such as *Synechocystic* sp., *Cyanothece* sp., *Microcoleus* sp., *Euhalothece* sp., and *Spirulina* sp. Some non-limiting examples of alkaliphilic algae strains include *Synechocystis salina, Aphanothece stagnina, Chamaesi-phon subglobosus, Rhabdoderma lineare, Synechococcus elongates, Phormidium ambiguum, Phormidium foveo-larum, Phormidium retzii, Oscillatoria splendid, Sscilla-toria limnetica, Spirulina fusiformis*, and *Spirulina laxissima*. However, any algae that can thrive at high pH values (>9.5) and withstand high (~60-100 mM) inorganic carbon content can be utilized.

Figure 2:
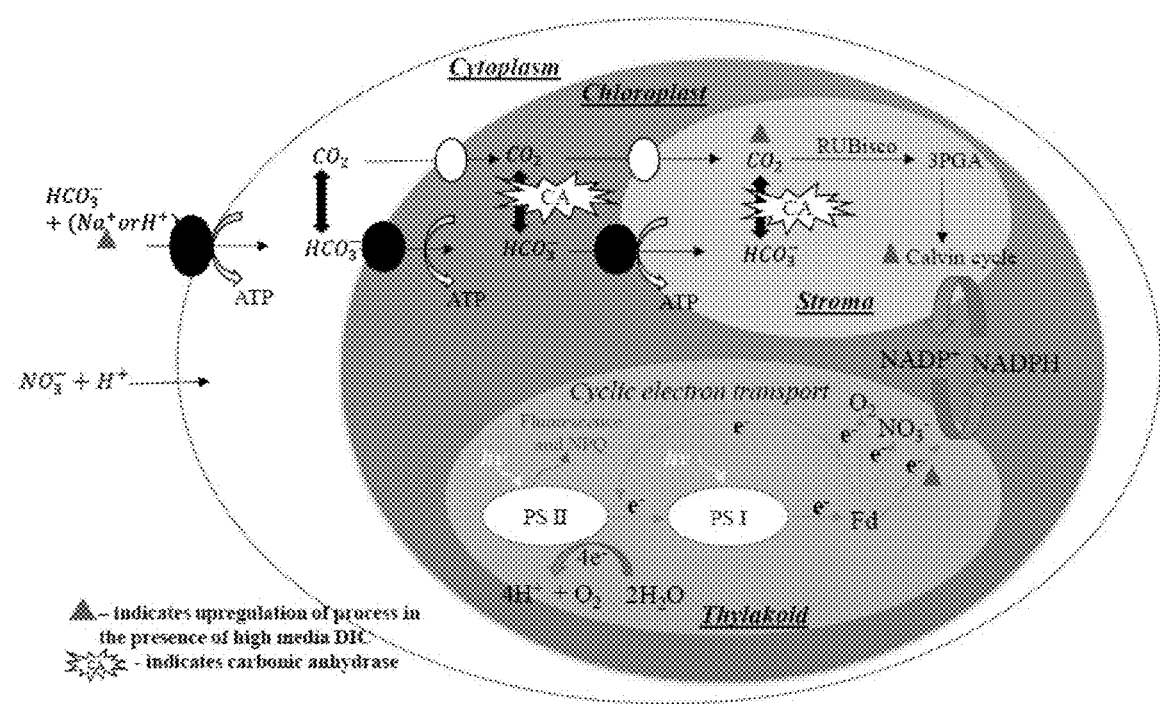
FIG. 2: Illustration depicting the cellular DIC transport and fixation mechanisms in alkaline media.

The multi-step process of DIC transport into alkaliphilic microalgae cells and ultimate conversion to organic carbon is shown in FIG. 2. The conversion to organic carbon using light energy (i.e., photosynthesis) takes place via two parallel processes: light-dependent and light-independent reactions (FIG. 2). The light-dependent reactions occur in the thylakoid region of cells with two photosystems (PS 1 and PS II) that work in tandem to produce energy (ATP) and reducing equivalents (NADPH). When a photon strikes chlorophyll within the photosystem, the absorbed energy is either used to split $H_2O$ (at PSII) and recover electrons (e⁻) or is dissipated as heat/fluorescence. The recovered e are transported through an electron transport chain (through ferredoxins, Fd) and used for generation of reducing equivalents (NADPH) or for nitrate reduction and protein synthesis (see the reactions below the dotted line, FIG. 2).

In parallel, under alkaline conditions, light-independent DIC uptake occurs via carbon concentrating mechanisms (CCMs) that consist of a series of active $HCO_3^-$ transporters, carbonic anhydrases, and, in some cases, conversions of C3 and C4 molecules (not depicted in FIG. 2 for simplicity). Since multiple enzymatic steps are involved, the DIC transport process can be kinetically limited by external DIC concentrations. In the presence of high DIC, the net flux through the transporters (shown as filled ovals in FIG. 2) is enhanced such that more DIC is available for carbonic anhydrases that can ultimately deliver $CO_2$ to RuBisCO at higher rates. The half-saturation constant for carbonic anhydrases is generally in the 20 mM range, and low DIC availability severely limits the kinetics of this enzyme. In addition, the carbonic anhydrase gene expression is low under low $HCO_3^-$ concentrations, which may decrease the availability of $CO_2$ at RuBisCO. Such a decreased availability of $CO_2$ at RuBisCO would negatively impact the rates of carbon fixation through the Calvin cycle. Simultaneously, the high cellular DIC flux drives the light-dependent reactions towards higher production of NADPH by increasing NADPH demand for use in carbon fixation. Thus, by maintaining high alkalinity, higher photosynthetic efficiencies and ultimately high rates of $CO_2$ fixation can be achieved.

The mechanisms of inorganic carbon uptake from the atmosphere and use for photosynthesis are (as described above) innately established in natural alkaline lakes which have the highest reported aquatic photosynthetic carbon fixation rates. In addition to facilitating sustained supply of $CO_2$ from the atmosphere (rather than flue gases), the use of high-pH and high-alkalinity media can enable the sustained cultivation of desired species due to the relatively low microbial diversity in these harsh environments. Grazer infestations are also less likely in alkaline environments. For example, *Daphnia* eggs lose viability when pH values exceed 10-10.5. In commercial practice, *Spirulina* production is successful, at least partly, due to the high pH growth conditions that enable prolonged maintenance of these cyanobacterial species in low-cost open ponds. A SLA-04 culture crash has not been observed despite several months of outdoor cultivation in high-pH and high-alkalinity media.

The adjustment of macro- and micro-nutrient concentrations results in improvements in carbohydrate and lipid productivity. One of the principal macro-nutrients important for algae cultivation is nitrogen (N). N is also a significant contributor to the net carbon footprint of algal biofuels. Low N is also very desirable for downstream conversion processes since the resulting fuels also have a low N content. Therefore, the cultivation of alkaliphilic algae on low N media was evaluated. The results showed that the high biomass productivities can be maintained at lower N in the media, and the resulting biomass also has a low N-content. An increase in pigment production (e.g., chlorophyll b) when cellular N content is high has been observed, which causes cultures to become "dark" and detrimental to light penetration. Overall, by adjusting media alkalinity and N supply, biomass with low N-content can be produced.

The requirements for the micro-nutrients Ca and Mg have also been evaluated, as the effects of these micro-nutrients are generally underappreciated in the art. Typically, these micro-nutrients are added at a concentration level of 5-7 mg/L (Bold's medium). However, under alkaline conditions their solubility in the medium is diminished. These reduced dissolved nutrient concentrations can induce "nutrient-limited stress" on the growing microalgae. It is known that N-starvation improves lipid productivity in microalgae. Therefore, whether micro-nutrient (Ca and Mg) limitations would also lead to improved biomass and lipid productivity during alkaliphilic microalgae cultivation was evaluated.

The impact of increasing medium salinity on biomass growth was also evaluated. Use of saline water (from oceans or from saline/brackish groundwater sources) improves the sustainability of microalgae cultivation by decreasing the requirements of freshwater. The results, described in the examples herein, indicate that cultivation of microalgae in high salinity media containing excess nitrogen and high biomass concentrations (i.e., conditions that limit light penetration into cultures), increased the production of phycocyanin—a high-value nutraceutical.

Recycled media can be used in the open ponds. In some embodiments, high concentrations (for example, 100 mM) of bicarbonate/carbonate salts are added to the culture media to provide high alkalinity. Hence, the ability to recycle and reuse the media is important to minimize the costs associated with replenishing these salts, and other unused nutrients. As described in the Examples herein, post-harvest media can be re-used without detrimental impact on biomass productivity.

The high pH media permits open-pond cultivation in "mixotrophic mode" without culture crash. In addition to facilitating sustained supply of $CO_2$ from the atmosphere (rather than from flue gases), the use of high-alkalinity and high-pH media can enable sustained cultivation of desired species, since it is likely that contaminating populations will be less diverse at higher pH values. A culture crash of the alkaliphilic strain SLA-04 has not been observed in the presently described method, despite a significant number of months of outdoor cultivation in high-pH and -alkalinity media. The extreme pH and alkalinity of the medium also allows for low-cost outdoor pond mixotrophic cultivation with significantly lower chance for bacterial contamination—mesophilic (<pH 8.5) outdoor cultivation woud likely not be possible with mesophilic algae.

It is understood that an open pond utilizing the methods described herein can include any apparatuses or structures common in open pond algae systems. For example, the open ponds may include paddle wheels or other water-moving devices usable to keep the algae circulating, as well as electronic controls, pumps, pipes, sensors, and the like. Continuous mixing of algal cultures is preferred in order to prevent thermal stratification and cell sedimentation, and to maintain carbonation. In some embodiments, the open ponds are known as raceway ponds, resembling a race track. A typical open pond is about one-foot deep, from about one acre to several acres in size, where the algae is exposed to natural solar radiation which is converted into biomass. An open pond system can be constructed out of any suitable material for containing the medium, such as PVC, PE, or concrete. Further, one skilled in the art will recognize that once the algae is harvested (such as by centrifugation), any method known in the art can be utilized to convert the harvested biomass to one or more high-value downstream products such as fuels, including hydrothermal liquefaction. In some embodiments, the biomass harvested from the open ponds as described herein can be converted to biofuels with lower nitrogen content than algae from conventional open ponds.

EXAMPLES

Example 1: Effect of $HCO_3^-$ Content on SLA-04

Biomass Growth and Productivity

The *Chlorella* sp. strain SLA-04 (henceforth referred to as SLA-04) was isolated from Soap Lake in the State of Washington (USA). Cultures were grown in a medium that comprises the nutrients: $NaNO_3$ (1.05 mM), $KH_2PO_4$ (0.3 mM), $MgSO_4 \cdot 7H_2O$ (0.3 mM), $CaCl_2 \cdot 2H_2O$ (0.17 mM), NaCl (0.42 mM), ferric ammonium citrate (10 mg/L)), and 1 mL trace metal solution. The trace metal solution comprised $H_3BO_3$ (9.7 mM), $MnCl_2 \cdot 4H_2O$ (1.26 mM), $ZnCl_2$ (0.15 mM), $CuCl_2 \cdot 2H_2O$ (0.11 mM), $Na_2MoO_4 \cdot 2H_2O$ (0.07 mM), $CoCl_2 \cdot 6H_2O$ (0.06 mM), $NiCl_2 \cdot 6H_2O$ (0.04 mM), $V_2O_5$ (0.01 mM), and KBr (0.08 mM). For experiments that were started in a mildly alkaline pH medium (8.7 and 8.2), $NaHCO_3^-$ was added as an inorganic carbon source at $HCO_3^-$ concentrations in the range of 7-40 mM. For pH-controlled cultures, pH was controlled by periodic $CO_2$ addition through a solenoid-regulated control system that maintained the pH at an approximate value of 8.7 (Neptune Systems Apex, NC, USA). (Experiment A.) For experiments that were started under significantly higher alkaline pH conditions (pH 10), equal molar concentrations of $NaHCO_3^-$ and $Na_2CO_3$ were added to achieve final $HCO_3^-$ concentrations of 4.5-30 mM. (Experiment B.)

Open raceway ponds with dimensions of 2'×1'×1' (L×W×D) were constructed and used in these experiments. These ponds were equipped with a real-time temperature and pH monitoring and data logging system (Neptune Systems Apex, NC, USA). The ponds were placed in a heated greenhouse. Tap water available at the greenhouse facility was first filtered through a 10 μm filter (to remove sediments) and then used for medium preparation. The working volume of the culture was kept at 5" for Experiment A and 6" for Experiment B.

Figure 3A:
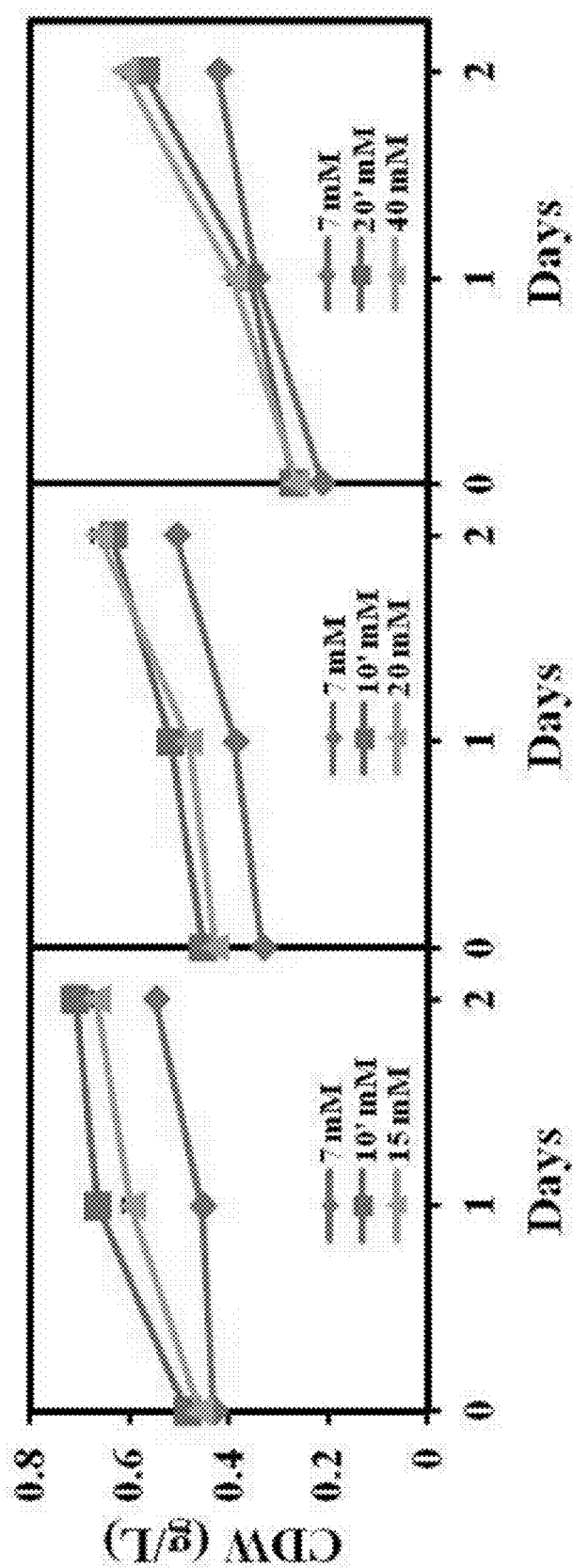
FIGS. 3A-3C: Graphs showing cell growth, biomass productivity, rapid light curve, and nitrate utilization parameters of SLA-04 grown under different inorganic carbon conditions (Experiment A).
Figure 3B:
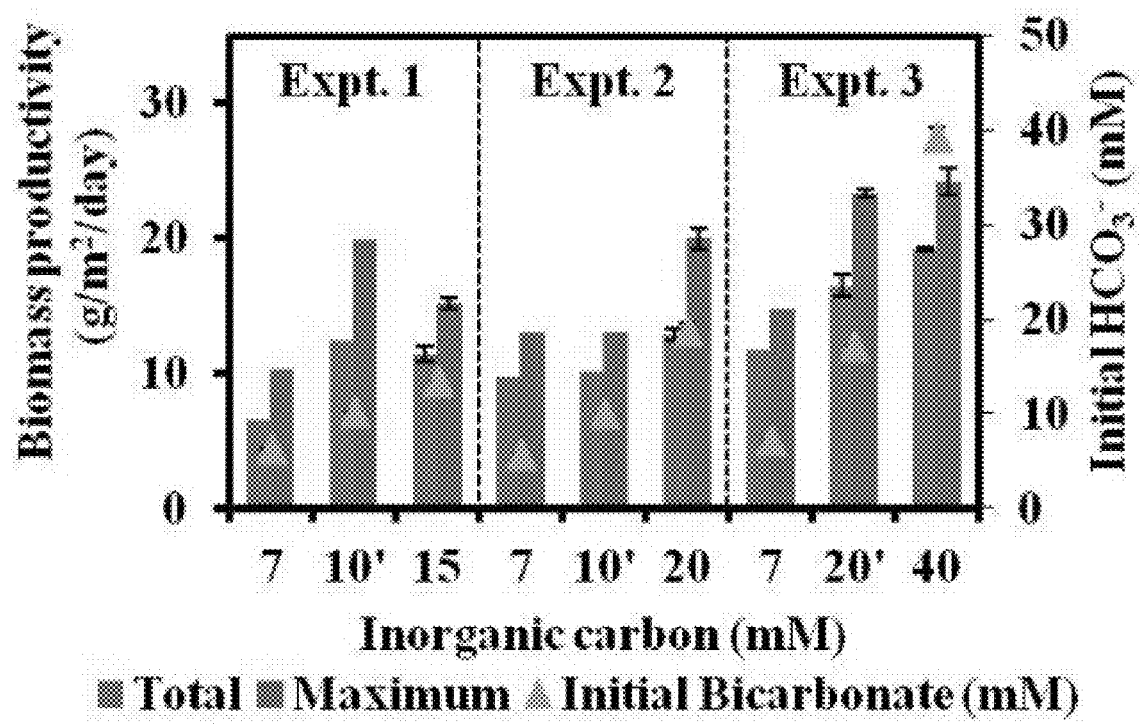

During Experiment A, biomass concentrations (measured as cell dry weight (CDW) and productivity of cultures grown in media with varying $HCO_3^-$ concentrations and without pH control were assessed and compared with pH-controlled controls (FIGS. 3A-3B). The results show that biomass concentrations as well as biomass productivity were greater when $HCO_3^-$ concentrations in the media were higher. Maximum biomass productivity was observed to be 24.2±1.0 g $CDW/m^2$/day for cultures that initially contained 40 mM $HCO_3^-$. These productivity values were similar (23.4±0.28 g $CDW/m^2$/day) to the productivities measured in pH-controlled cultures containing 20 mM $HCO_3^-$ (FIG. 3A).

Because of CCMs, microalgae can accumulate $HCO_3^-$ in cytosol and subsequently deliver high $CO_2$ concentrations around the ribulose-1,5-bisphosphate carboxylase oxygenase (RuBisCO) enzyme, and thus increase the rates of photosynthetic carbon fixation (FIG. 2). However, the $HCO_3^-$ transfer rate into cells is an important factor to maintain high cytosolic $HCO_3^-$ concentration as well as photosynthetic rate. Higher media concentrations of $HCO_3^-$ lead to improved mass transfer rates and cellular uptake.

Figure 3C:
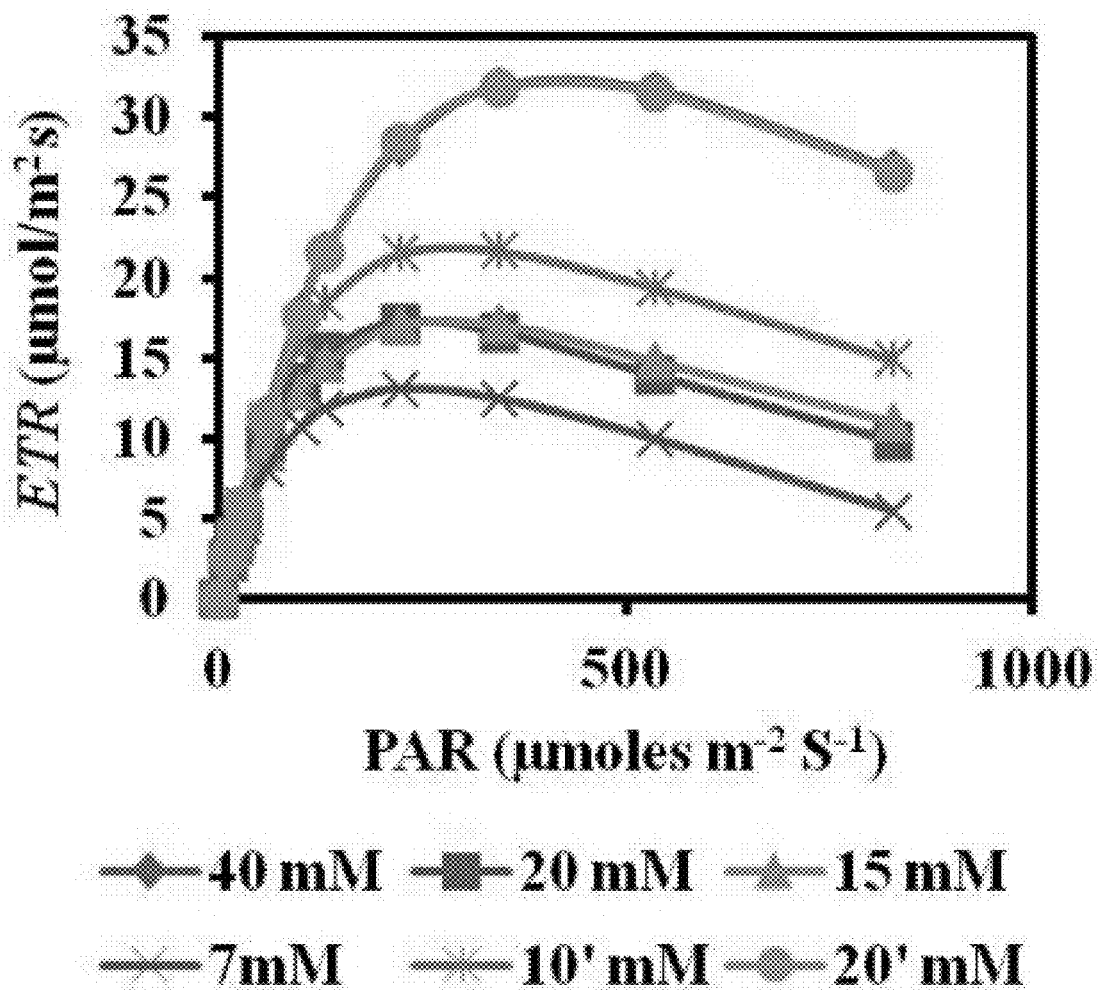

To assess the impact of $HCO_3^-$ on photosynthetic efficiency (i.e., the efficient use of incident photons), "rapid light curve" measurements were made. As shown in FIG. 2, only a portion of the electrons generated from the incident light are utilized towards photosynthesis while the rest are dissipated. The electrons participating in photosynthesis serve to electrochemically reduce cellular DIC to carbohydrates via NADPH mediated reactions at RuBisCO (FIG. 2). The flow of electrons towards photosynthesis is referred to as the "electron transfer rate" (ETR). Higher values of ETR were observed in cultures containing higher concentrations of bicarbonate in the media (FIG. 3C). Cultures fed with high $HCO_3^-$ content (40 mM) showed a maximum ETR value ($ETR_{max}$) of 32 $\mu mol/m^2 s$, while cultures fed with 7 mM $HCO_3^-$ showed much lower $ETR_{max}$ values of 13 $\mu mol/m^2 s$ (FIG. 3C). Overall, the higher alkalinity medium allowed better photon utilization.

pH Change

Figure 4A:
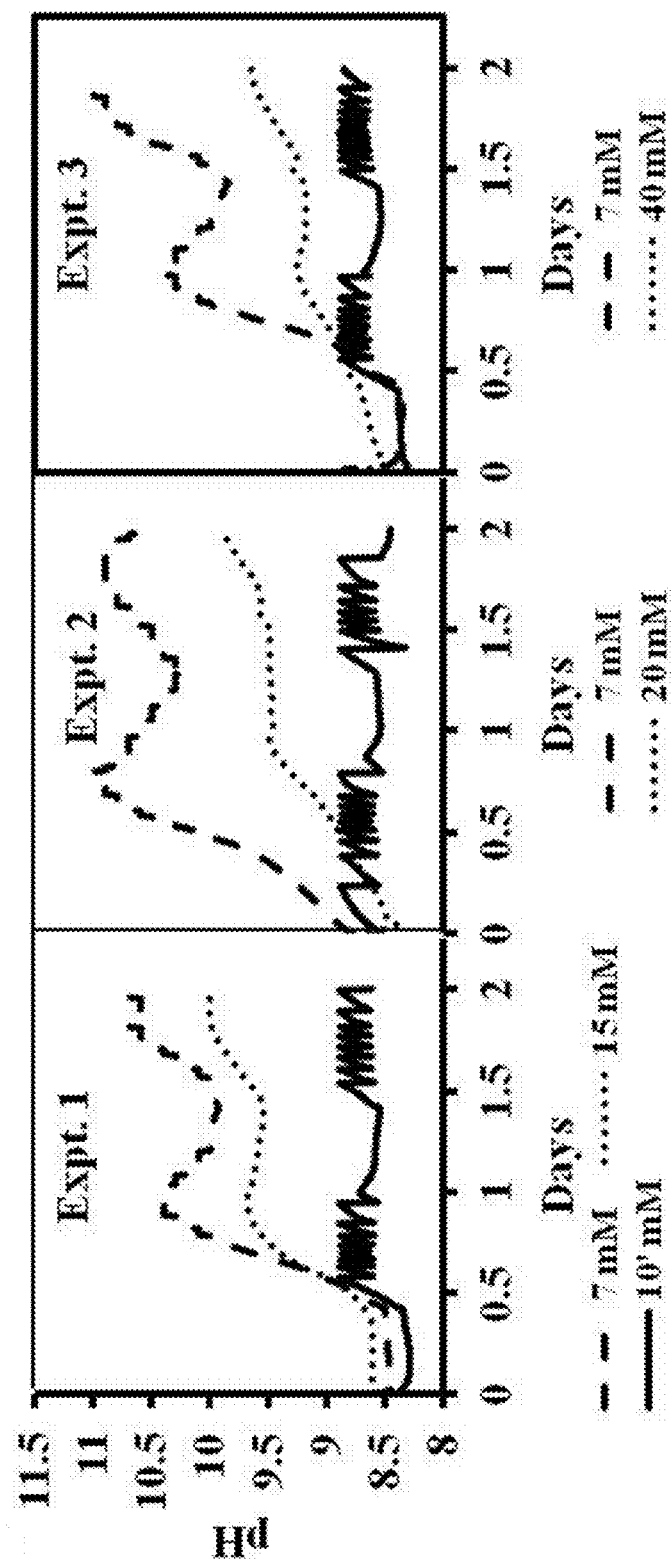
FIGS. 4A-4B: Graphs showing pH change during SLA-04 growth (FIG. 4A), and for Experiment A (FIG. 4B).

An increase in pH was observed during algal growth at day time (light cycle) due to uptake of bicarbonate and release of hydroxyl ions (Eq 7). pH decreased at night due to $CO_2$ release from microalgae respiration (FIG. 4A).

Figure 4B:
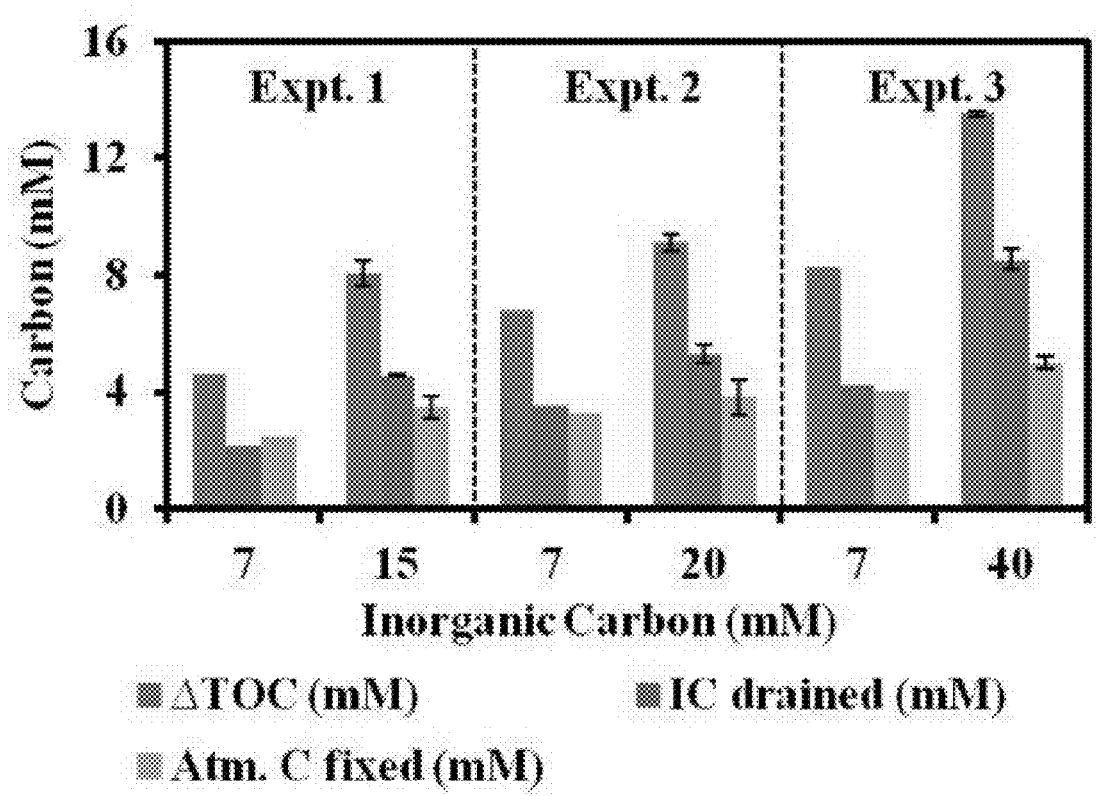
Figure 5A:
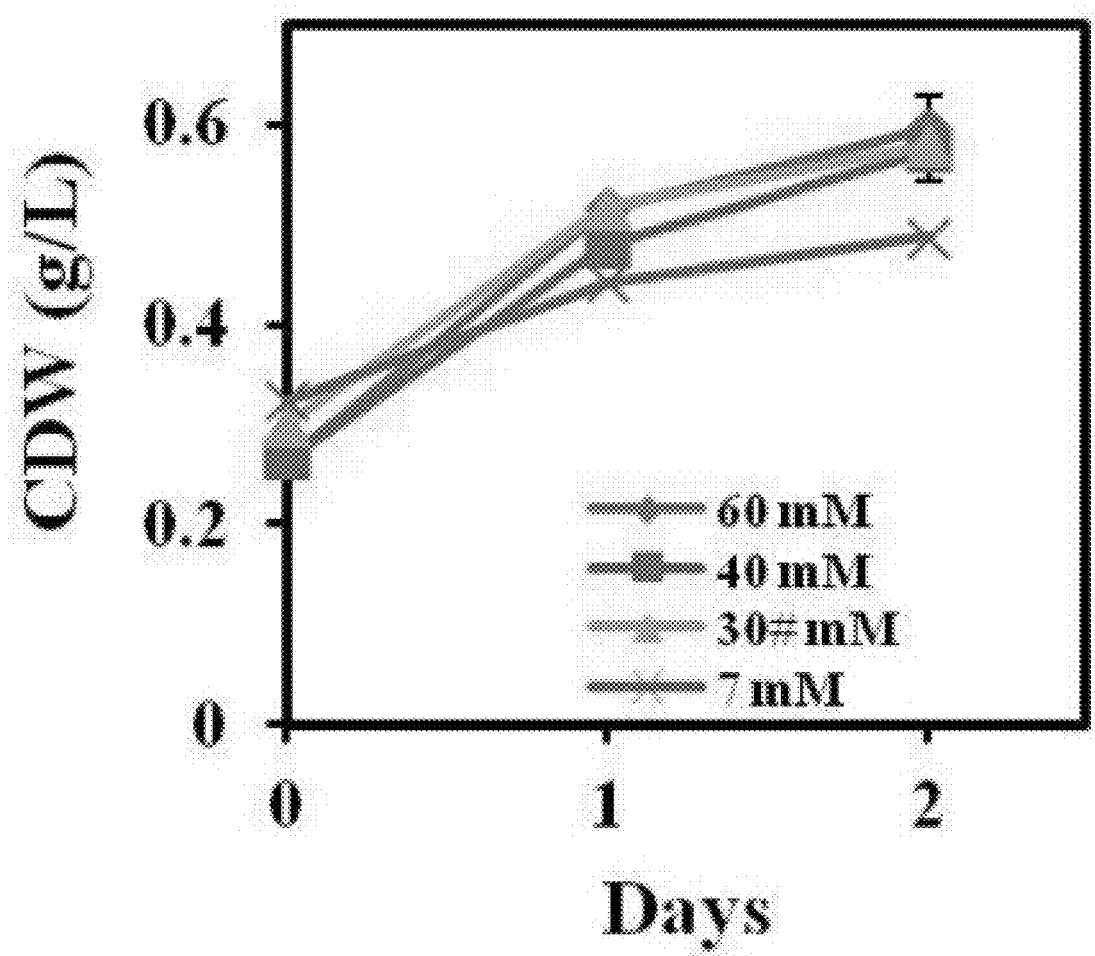
FIGS. 5A-5C: Graphs showing cell growth, biomass productivity, rapid light curve, and nitrate utilization parameters of SLA-04 grown under different pH and inorganic carbon conditions.
Figure 5B:
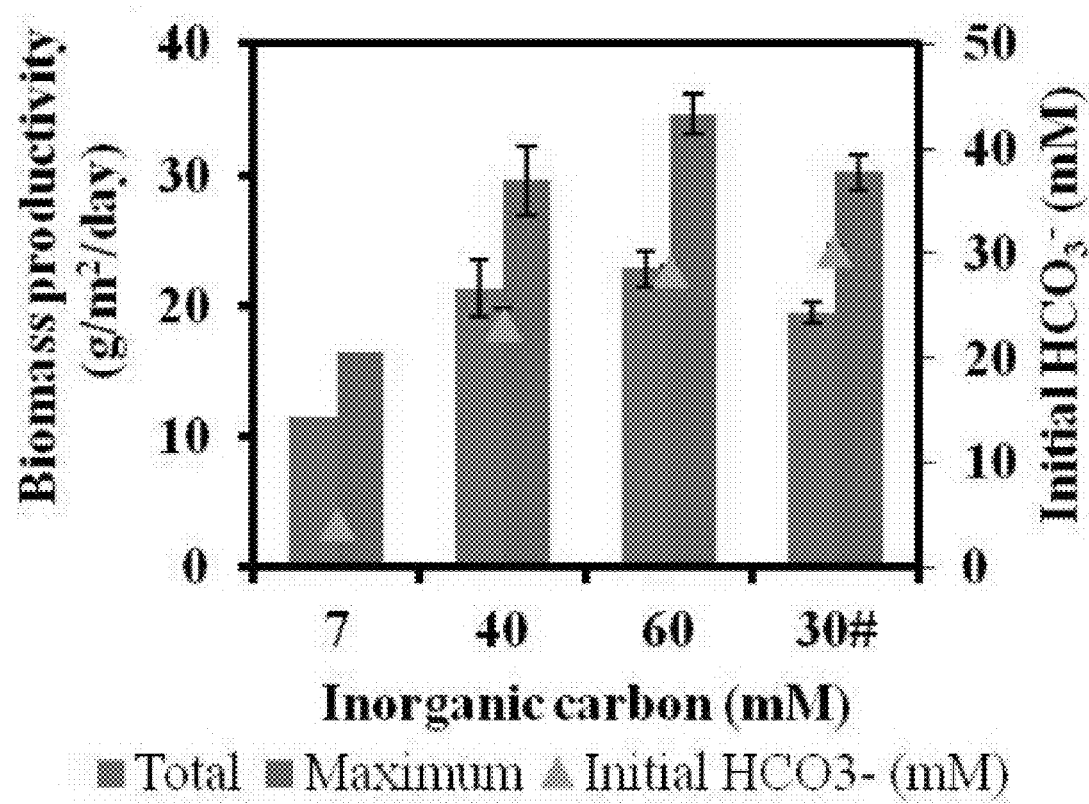
Figure 5C:
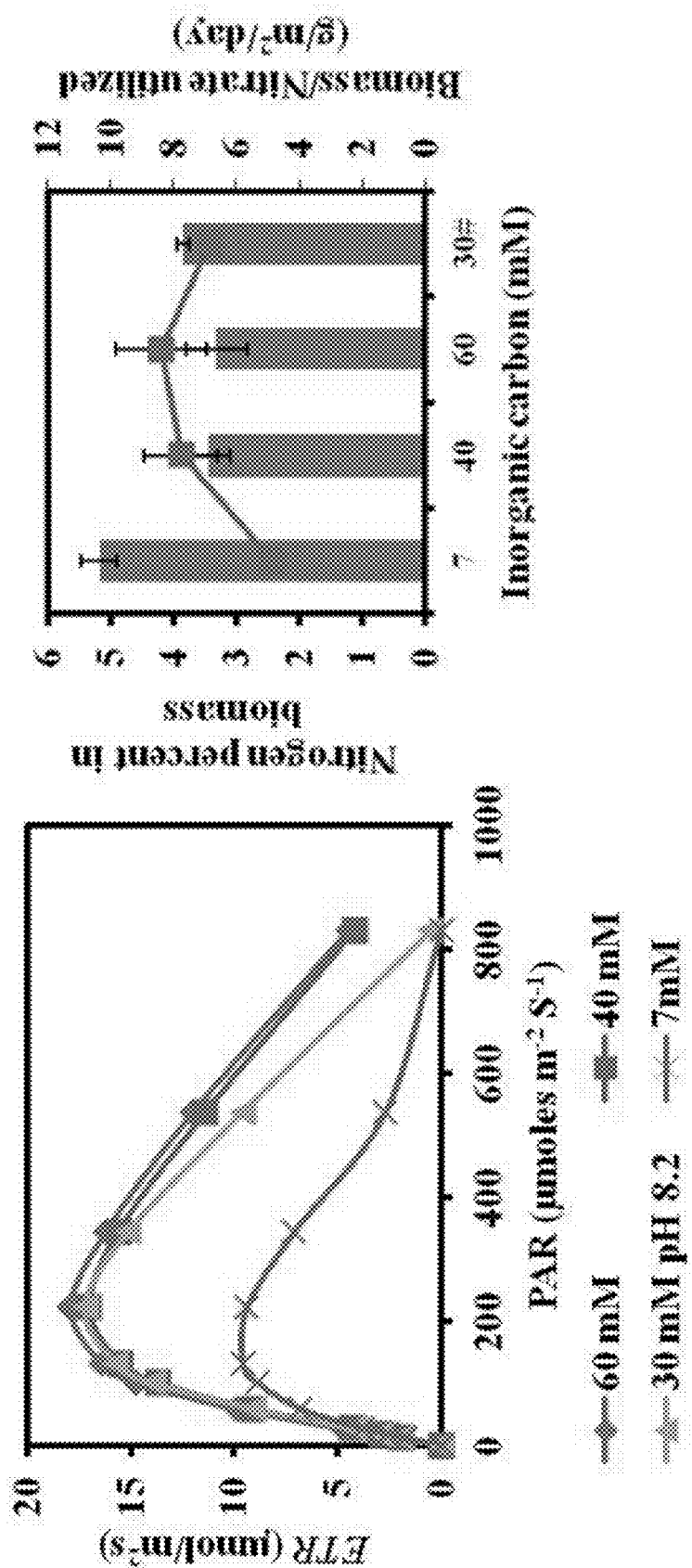
Figure 13A:
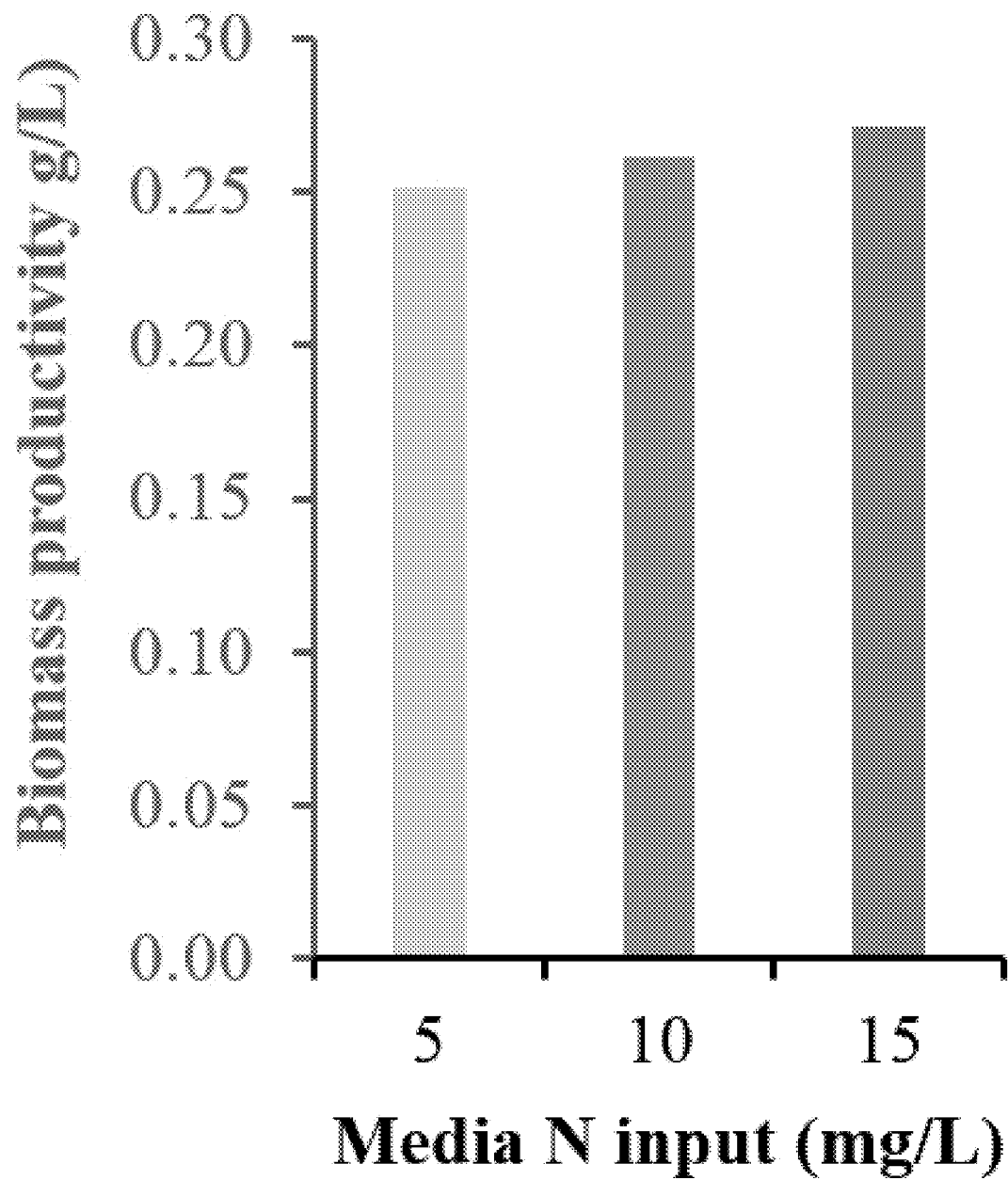
FIGS. 13A-13B: Biomass productivity for cultures grown in different N concentrations (FIG. 13A), and chlorophyll concentration for cultures grown in different N concentrations (FIG. 13B), given biomass productivity for two days' period.
Figure 13B:
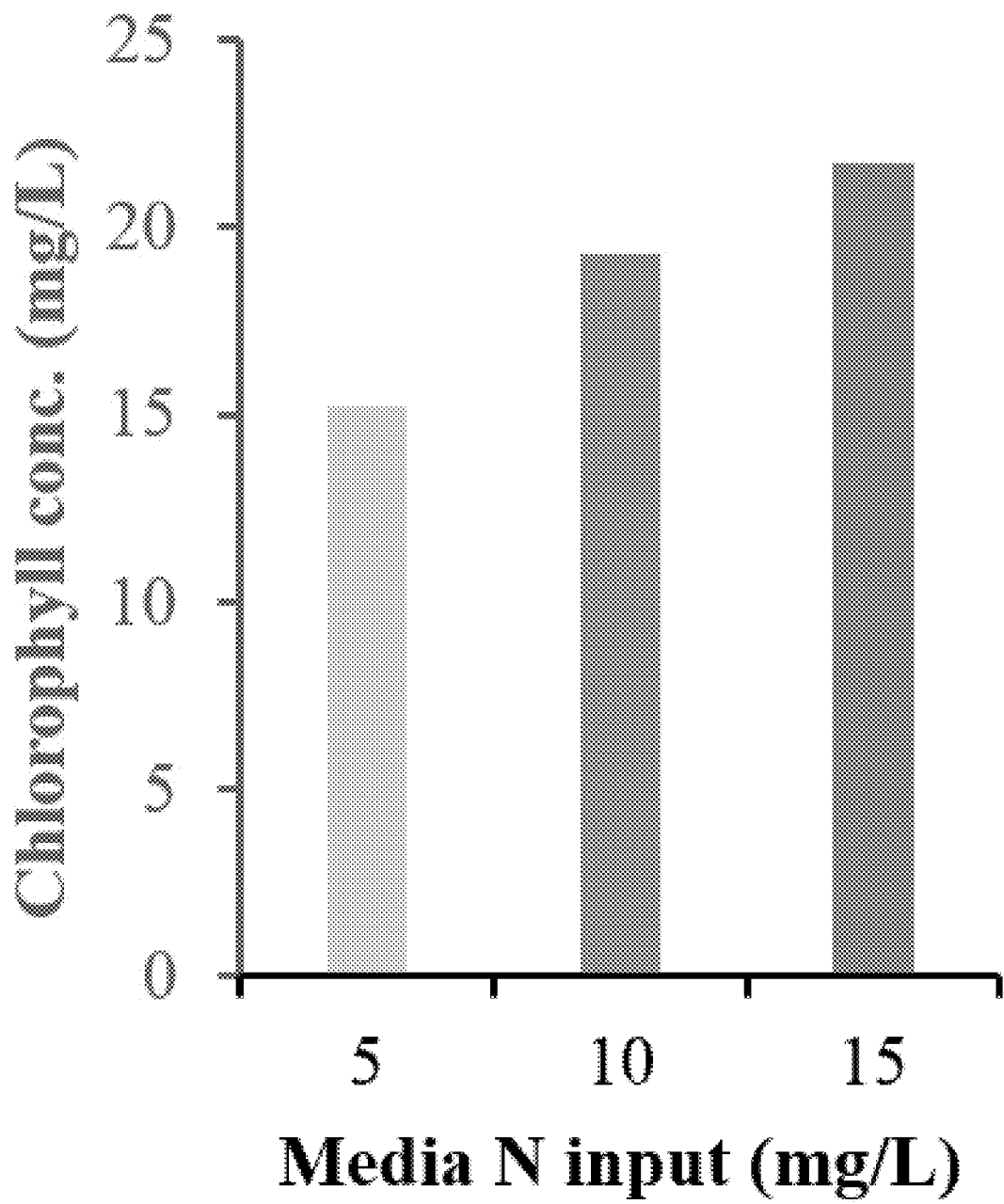

Example 2: Biomass Growth and Productivity in High-pH Media with Varying Levels of Alkalinity Biomass Growth, Productivity Experiment B was performed to assess biomass productivity at high pH. Since Experiment A (FIGS. 3-4) showed improvement in productivity with higher alkalinity, a similar approach was used in Experiment B and media alkalinity was varied. Experiment B was performed in media initially at pH 10. The alkalinity of the media was set such that initial bicarbonate concentrations were 7, 20, and 30 mM. An experiment at an initial pH of 8.2 and initial $HCO_3^-$ concentration of 30 mM served as a control. FIGS. 5A-5C depict the growth, productivity, and ETR of SLA-04 cultures during Experiment B. As observed in Experiment A (Example 1), biomass growth, productivity, and ETR increased when $HCO_3^-$ concentration in medium increased. The results revealed that with the same $HCO_3^-$ availability (30 mM), cultures started with higher pH (9.9) showed higher growth as well as maximum productivity (34.7±1.5 g CDW/ m²/day) than cultures started with low pH (8.2) (FIGS. 5B, 5C). Table 1 (FIG. 13) shows that when compared to low $HCO_3^-$ conditions, the parameters related to efficient energy capture towards carbon fixation were higher, and the parameters related to energy dissipation were lower under high $HCO_3^-$ conditions.

TABLE 1

Rapid light curve parameters for cultures grown under high and low $HCO_3^-$ concentrations.

| | Description | Parameter | High $HCO_3^-$ (30 mM) | Low $HCO_3^-$ (7 mM) |
|---|---|---|---|---|
| Energy capture towards carbon fixation | Effective PS II quantum yield | Y (II) | 0.361 | 0.209 |
| | Maximum electron transfer rate (µmol/m²s) | $ETR_{max}$ | 17.9 | 9.4 |
| | Photosynthetic efficiency (el./ph.) | α | 0.167 | 0.098 |
| | Light saturation (µmol/m²s) | $I_k$ | 126 | 96 |
| Energy dissipation | Quantum yield of regulated energy dissipation | Y (NPQ) | 0.066 | 0.094 |
| | Quantum yield of non regulated energy dissipation | Y (NO) | 0.573 | 0.697 |

Nitrate utilization efficiency (g biomass/g nitrate utilized) was observed to be higher in cultures with high $HCO_3^-$ availability (FIG. 5D), resulting in low nitrogen content in the biomass. This is important to produce low nitrogen content biofuels from biomass intermediates through hydrothermal liquefaction (HTL). Moreover, it reduces the cost and greenhouse gas emissions associated with industrial nitrate production.

pH Change, and Atmospheric $CO_2$ Capture

Figure 6A:
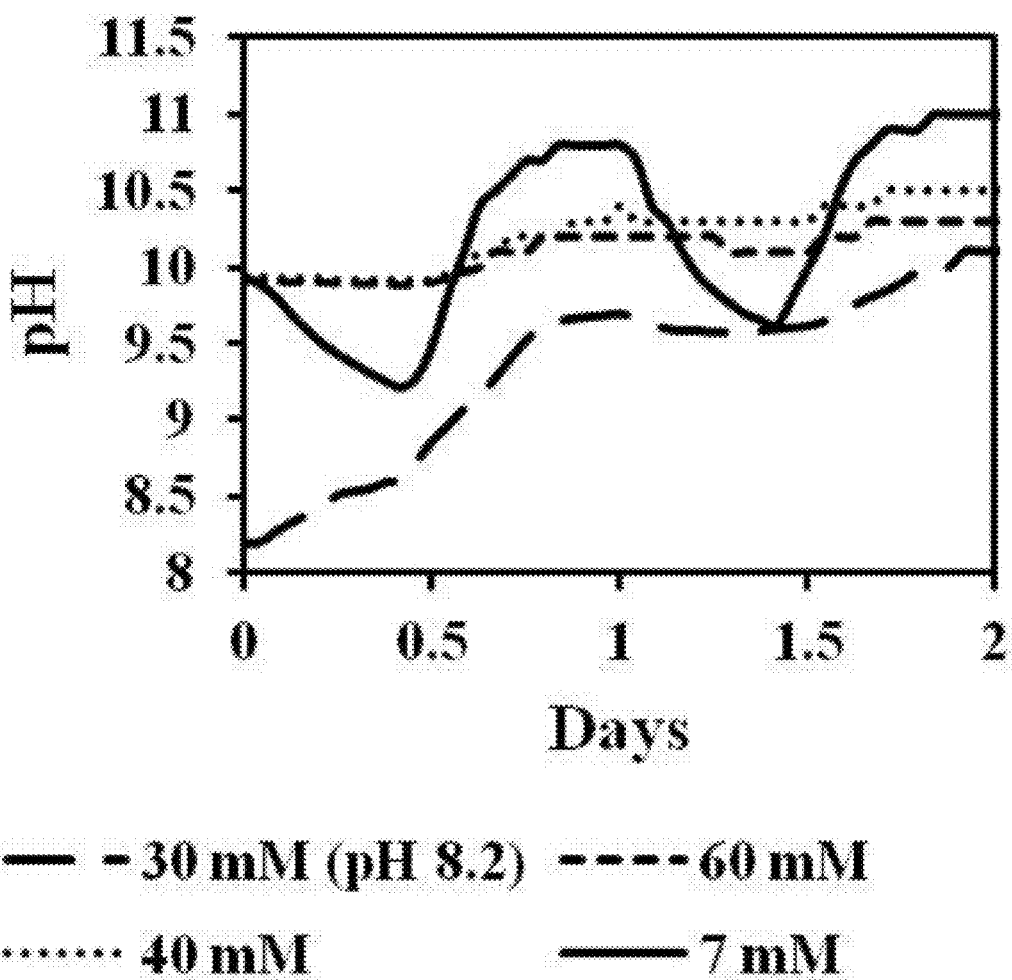
FIGS. 6A-6B: Graphs showing pH change during SLA-04 growth (FIG. 6A) and carbon balance of SLA-04 growth system (FIG. 6B).

Change in pH during algal growth is illustrated in FIG. 6A. Cultures fed with high $HCO_3^-$ content showed higher buffering capacity than cultures fed with low $HCO_3^-$ content. Detailed $OH^-$ increase and controlled mechanisms are shown in Table 2.

TABLE 2

$OH-$ ion balance of SLA-04 grown under different pH and inorganic carbon conditions.

| | | $OH^-$ Control mechanisms | | | |
|---|---|---|---|---|---|
| Inorganic carbon (mM) | Increase in $OH^-$ conc. (mM) | Atm. $CO_2$ absorption (mM) | $HCO_3^-$ to $CO_3^{2-}$ conversion (mM) | Δ $OH^-$ (mM) | Atm. $CO_2$ absorption/ $HCO_3^-$ to $CO_3^{2-}$ conversion |
| 7 | 6.74 | 5.26 | 0.56 | 0.91 | 9.33 |
| 40 | 12.39 | 6.06 | 6.10 | 0.23 | 1.00 |
| 60 | 13.44 | 7.62 | 5.70 | 0.12 | 1.34 |
| 30 pH 8.2 | 11.35 | 2.46 | 8.77 | 0.12 | 0.28 |

Figure 6B:
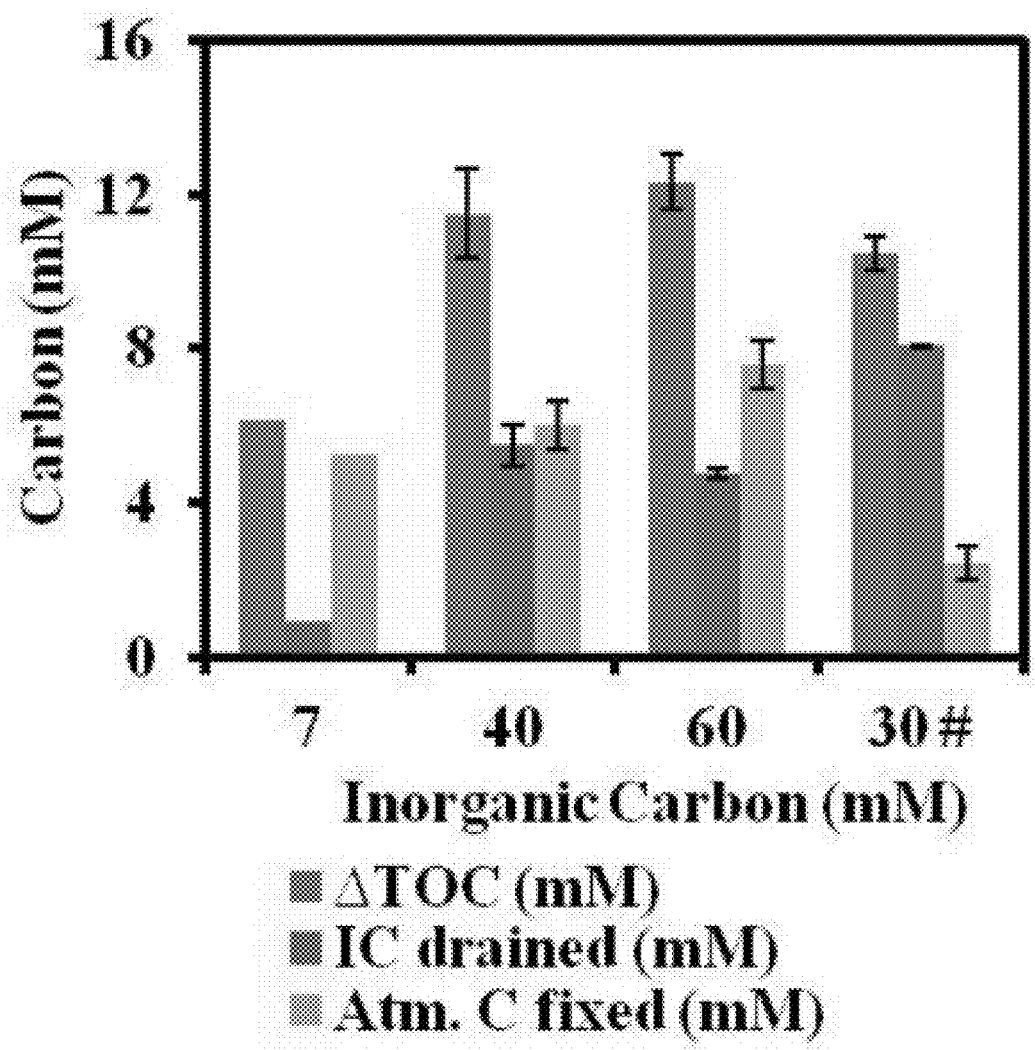
Figure 7:
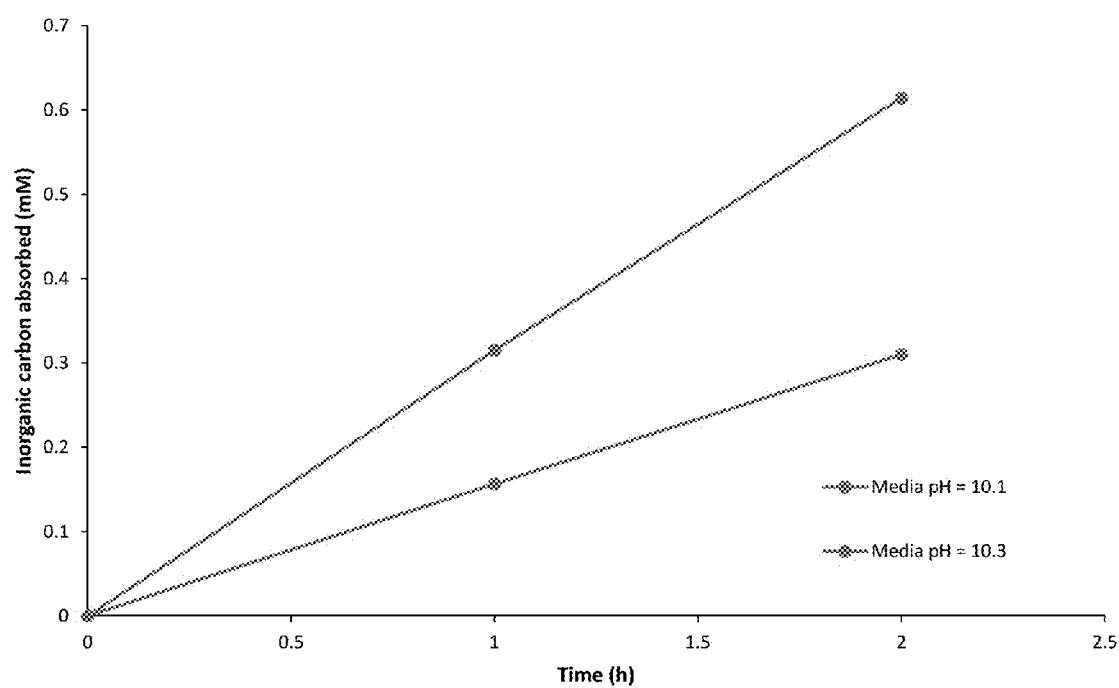
FIG. 7: Graph showing $CO_2$ absorption under abiotic (without algae) conditions.

Note:
Increase in $OH-$ concentration generated was calculated from sum of increase in TOC and $NO_3^-$ and phosphate utilization data. Increase in $CO_3^{2-}$ indicates $HCO_3^-$ to $CO_3^{2-}$ conversion. Atm. $CO_2$ absorption was calculated by: Atm. $CO_2$ absorption = $OH^-$ generation − $HCO_3^-$ to $CO_3^{2-}$ conversion + Δ$OH^-$ The data indicate that with the same initial inorganic carbon availability (60 mM), cultures started with pH 9.9 showed higher (1.34) atm. $CO_2$ absorption/$HCO_3^-$ to $CO_3^{2-}$ conversion than cultures started with pH 8.2 (0.28). These results indicate that under high pH algal growth conditions, atmospheric $CO_2$ absorption dominates over $HCO_3^-$ to $CO_3^{2-}$ conversion and results in low inorganic carbon drain. Carbon content of dried biomass was observed to be in the range of 44-47%. FIG. 5B depicts the carbon balance data for all cultures. Maximum ΔTOC (12.3±0.7 g C/m²) was observed in cultures fed with high inorganic carbon content (60 mM). For these cultures, the inorganic carbon drain ΔIC was observed to be 4.75±0.13 g C/m², revealing that the remaining 61% (7.55±0.61 g C/m²) of biomass carbon was derived from atmospheric $CO_2$ absorption (FIG. 6B). The Example 1 and 2 results demonstrate that increasing initial pH from 8.7 to 9.9 results in an increase in atmospheric $CO_2$ fixation in biomass from 37% to 61%.

Figure 8A:
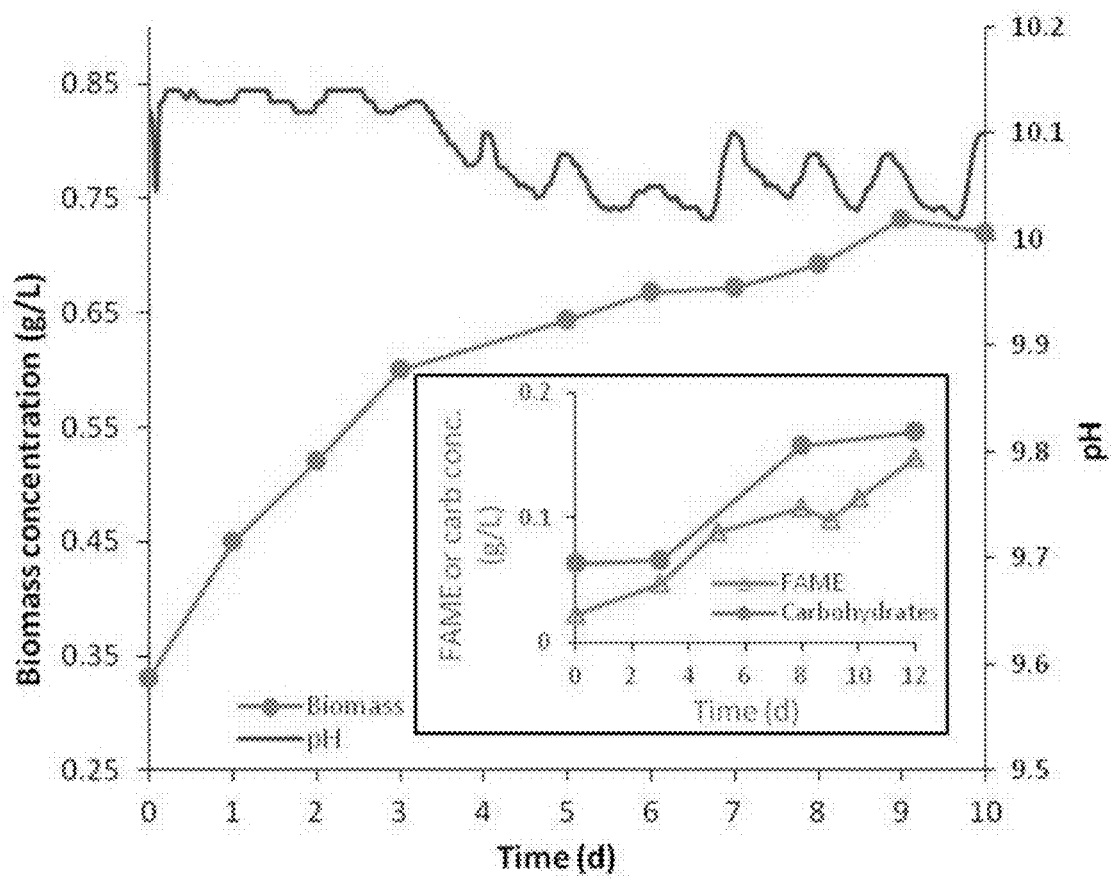
FIGS. 8A-8B: Results of phototrophic SLA-04 outdoor (750 L) raceway pond cultivation (FIG. 8A), and carbon balance for cultures grown under phototrophic conditions (FIG. 8B).
Figure 8B:
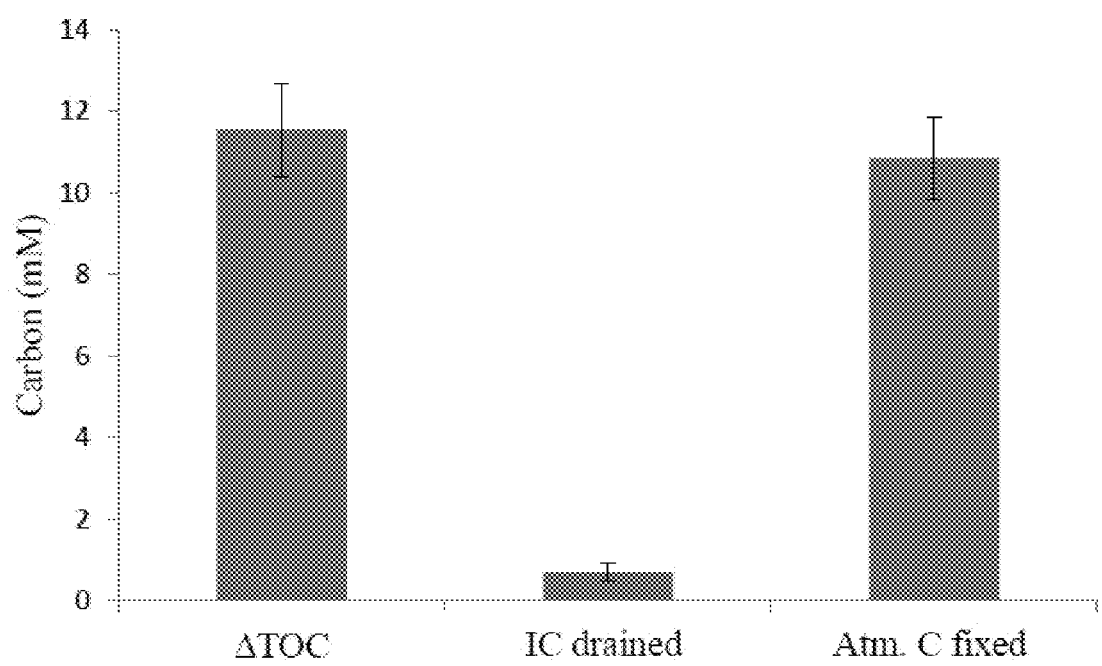
Figure 9:
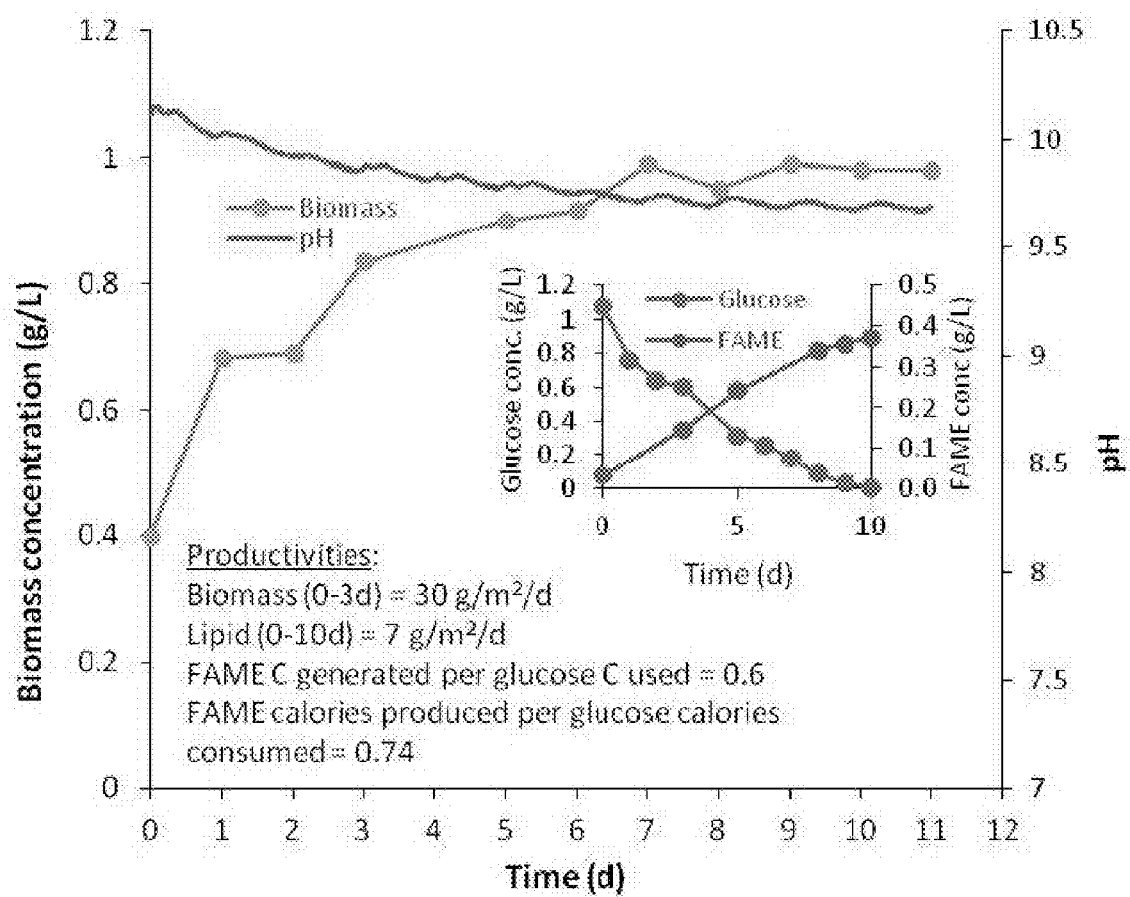
FIG. 9: Results of mixotrophic cultivation of SLA-04 outdoor (750 L) raceway pond cultivation.

Example 3: Phototrophic and Mixotrophic Cultivation of Microalgae Under High pH and Alkalinity Sustainability of microalgal cultivation under phototrophic and mixotrophic conditions was studied in 1100 L ponds with efficient mixing by paddle wheel (Commercial algae Professionals, NC, USA) with a working volume of 750 L and a depth of 7" in outdoor raceway ponds under high pH (~10) and high inorganic carbon (~100 mM) conditions without $CO_2$ supplementation. Under the phototrophic conditions, cell dry weight, and biomass and lipid productivities, were determined to be 23 g/m²/day and 2 g/m²/day, respectively (FIG. 8A). The results indicate that ~95% of the biomass carbon was derived from atmospheric $CO_2$, rather than from the added inorganic carbon (FIG. 8B). This shows that when compared to Example 2, the results demonstrate that efficient mixing of the culture medium improved atmospheric $CO_2$ derived biomass carbon from 61% to 95%. Under mixotrophic cultivation with glucose, SLA-04 cultures grew without any measurable signs of contamination and showed significantly higher biomass productivity (57 g/m²/day) due to the availability of additional organic carbon and associated reducing equivalents (FIG. 9). Lipid productivities were also higher under mixotrophic conditions (7 g/m²/day) relative to phototrophic SLA-04 cultures (2 g/m²/day) (FIG. 9).

Example 4: Remnant Media Nutrients Recycling

Figure 10:
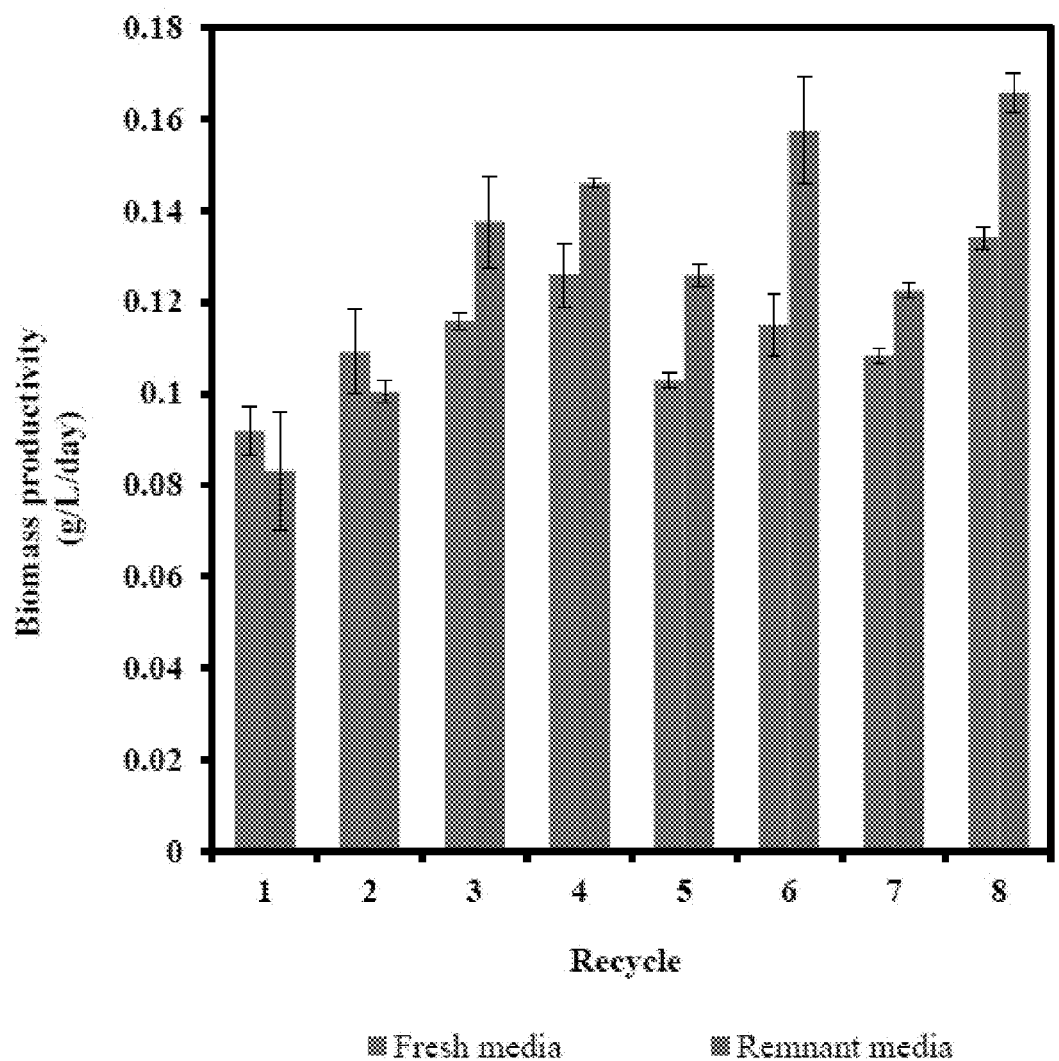
FIG. 10: Graph showing biomass productivity under fresh and recycling media conditions.

After growth, remnant media was recovered by harvesting the algal biomass through centrifugation. Then, the effect of remnant media (which contain high amount of inorganic carbon (~60 mM)) on biomass growth was evaluated by adding the used portion of nutrients only. The remnant media was recycled 8 times without any deleterious effects on algal biomass growth. FIG. 10 depicts a comparison between algal biomass growth pattern using remnant media and fresh media.

Example 5: Nitrogen Utilization by SLA-04 and the Effect of N Input on SLA-04 Biochemical Composition Nitrogen is a macronutrient and N content in biomass can determine the end-use of microalgae. For instance, high N-content (i.e., high protein) is desirable for microalgae use as food/feed ingredient. However, for biofuel production low N in biomass is desirable since presence of N in fuel is detrimental to fuel quality. Conventional cultivation methods use high concentration of N in the medium, which leads to production of biomass with high N content. The concentration of these nitrogenous compounds in the biomass can be decreased by growing microalgae under nitrogen limitation conditions. But severe nitrogen limitation can also impair growth. It was demonstrated that by maintaining an optimal concentration of N in the media, the N-content of biomass can be decreased without significant detrimental impact on biomass productivity.

Figure 11:
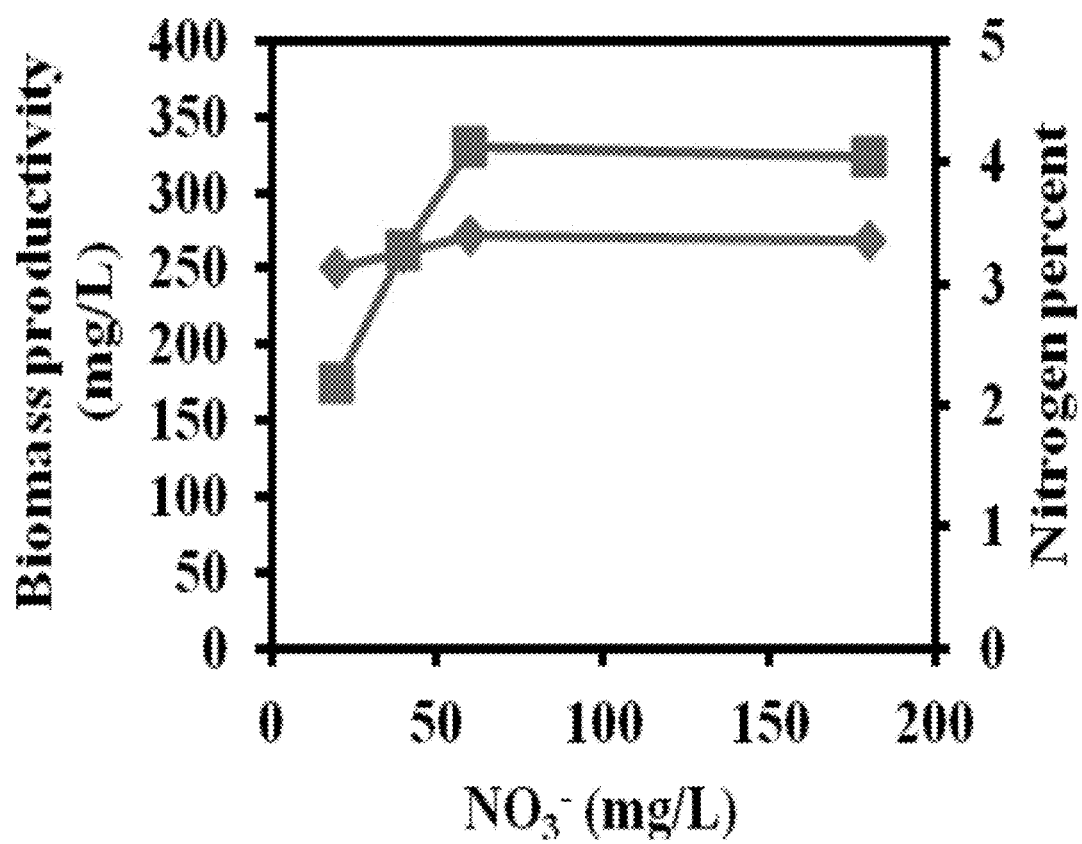
FIG. 11: Graph showing the effect of initial nitrate concentration on nitrogen percent of harvested biomass.

The results from 450 mL e-PBR experiments (FIG. 11) show that the high biomass productivities can be maintained at lower N in the media. The resulting biomass also has a low N-content (FIG. 11).

Additional indoor experiments were performed with SLA-04 cultures grown in 3 L reactors. Cultures were grown in a medium that comprised the nitrogen concentration in the range of 5-15 mg/L using $NaNO_3$ as a nitrogen source. $NaHCO_3^-$ and $Na_2CO_3$ were added in a molar ratio of 2:3 to get a final $HCO_3^-$ concentration (30 mM) and initial pH 10.1. Cultures adapted to high media N input (27 mg/L) with initial nitrogen content in biomass about 7% was used as an inoculum. The reactors were placed on a stir plate and illuminated by a bank of 4 Ecolux Starcoat 54 W fluorescent tubes (GE Lighting, Cleveland, Ohio) on each side. Light cycle was maintained at a PAR intensity ~400 µmol/m²/s on each side for 10 h.

The results (3 L reactors) show that the high biomass productivities can be maintained even at N content 5 mg/L in the media (FIG. 13A) because the low N availability avoids excess production of nitrogen storage compounds (e.g., for pigments). Also, an increase in chlorophyll pigment production (FIG. 13B) was observed when medium nitrate content was high, which causes cultures to become "dark" and detrimental to light penetration. The results indicate all the cultures were photosynthetically active, however there is no significant difference in photosynthesis efficiency ($F_v/F_m$) and maximum electron transfer rate ($ETR_{max}$) when N availability for the culture is decreased (Table 3).

TABLE 3

Rapid light curve parameters for cultures grown in 3 L reactors and under different $NO_3$ concentrations (time = 2 days).

| Media N input (mg/L) | Fv/Fm | $ETR_{max}$ PSII (µmol/m²s) |
|---|---|---|
| 5 | 0.649 | 17.6 |
| 10 | 0.685 | 17.7 |
| 15 | 0.711 | 19.1 |

Note:
Fv/Fm: maximal PS II quantum yield; $ETR_{max}$ PSII: Maximum electron transfer rate (µmol/m²s).

Example 6: Nitrogen Utilization by SLA-04 and the Effect of N Input on SLA-04 Biochemical Composition—Outdoor Experiments at 30 L Scale The outdoor experiment was conducted as a follow-up experiment to the indoor experiment with the same media conditions to examine the application of low-N, high-productivity cultivation in open ponds. Initial media N input was adjusted to a range of 5-27 mg/L using sodium nitrate as a nitrogen source. In contrast to the indoor experiments, cultures were first adapted to experimental nitrogen conditions for ten batches to get constant N content in biomass relative to the media N input. Then the experiments were conducted in open raceway ponds (30 L) with working volume of 20 L and performed in sequential batches, with each batch lasting for a duration of two days.

Figure 14A:
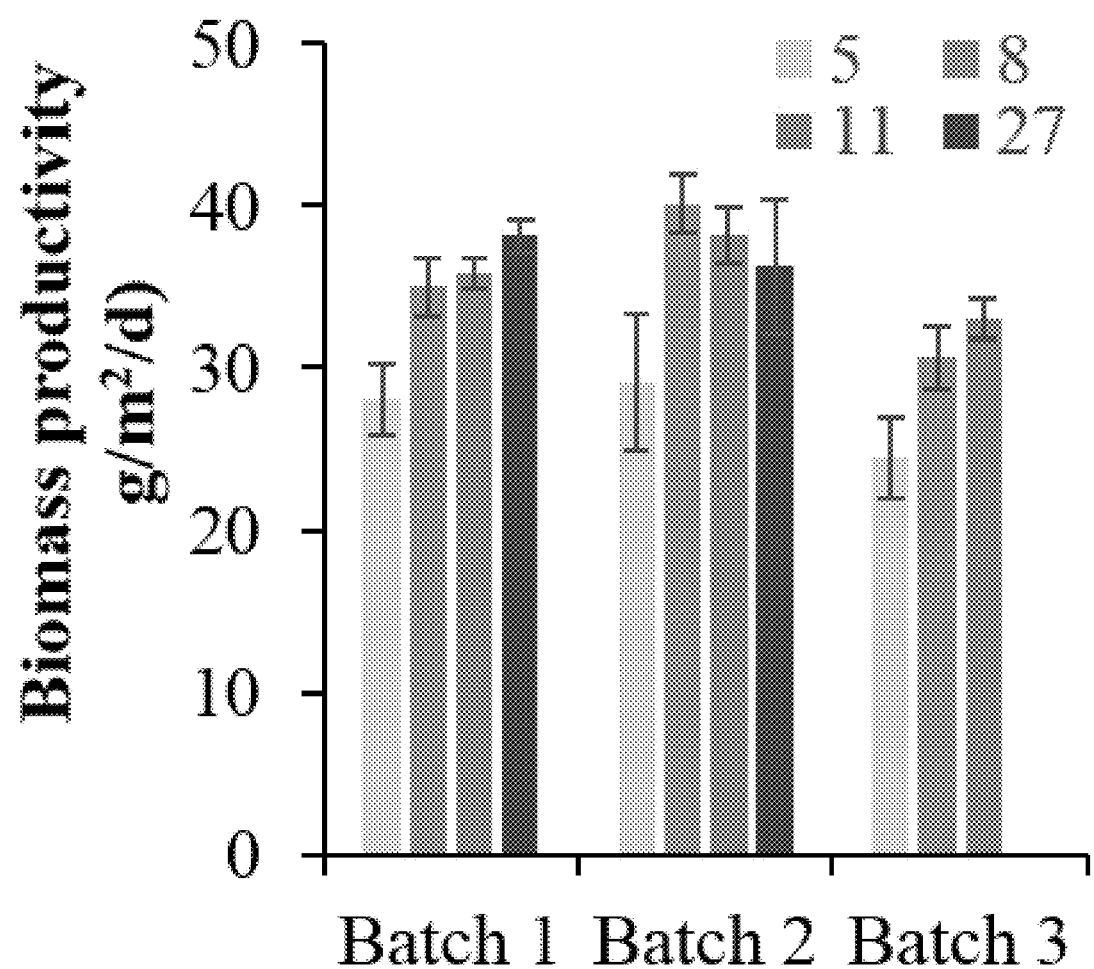
FIGS. 14A-14F: Effect of media N input on SLA-04 cultures in 30 L reactors.
Figure 14B:
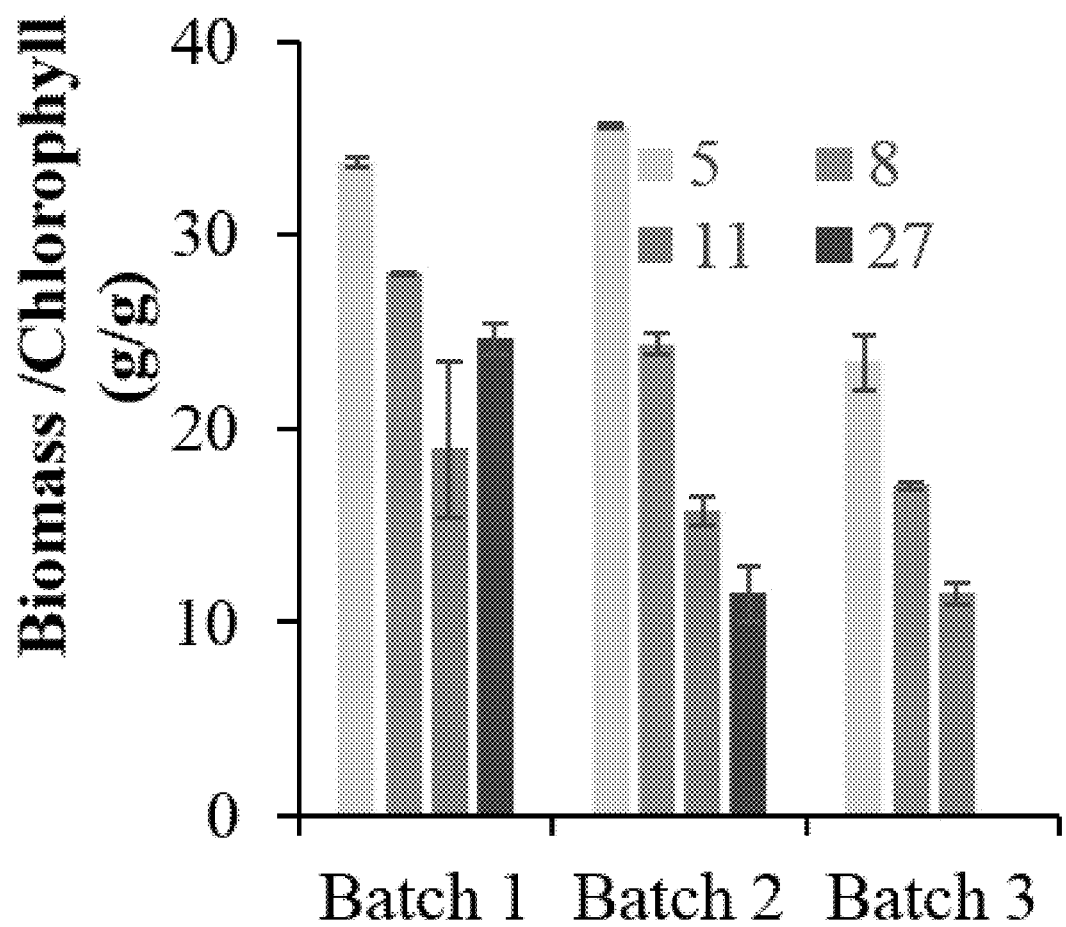
Figure 14C:
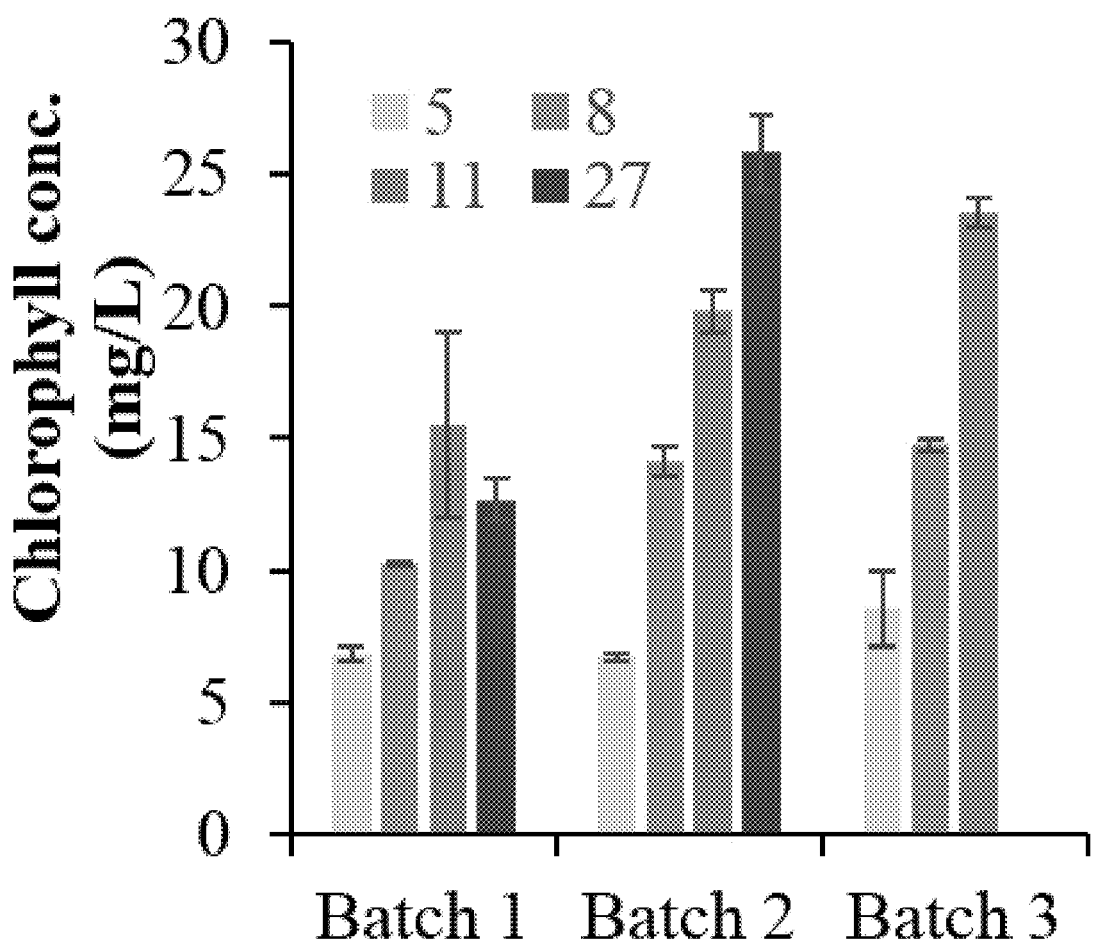
Figure 14D:
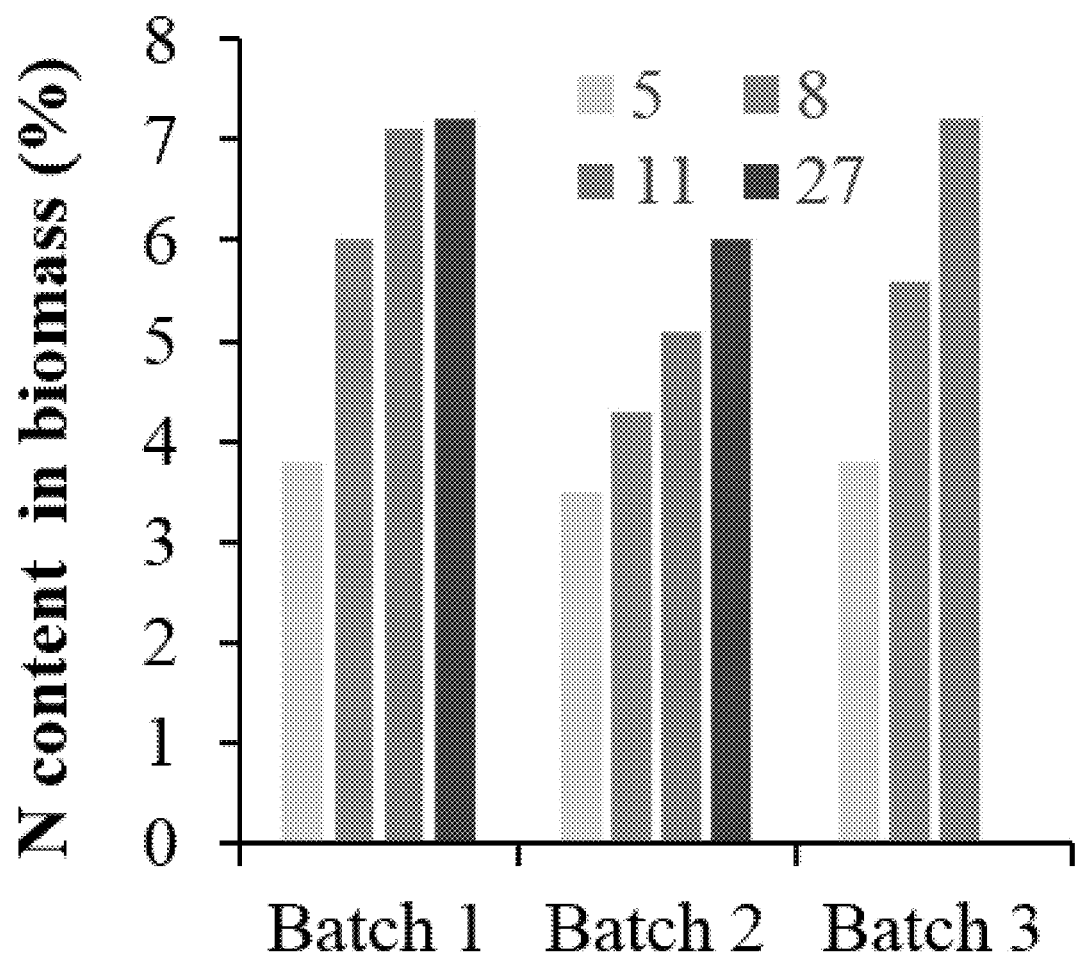
Figure 14E:
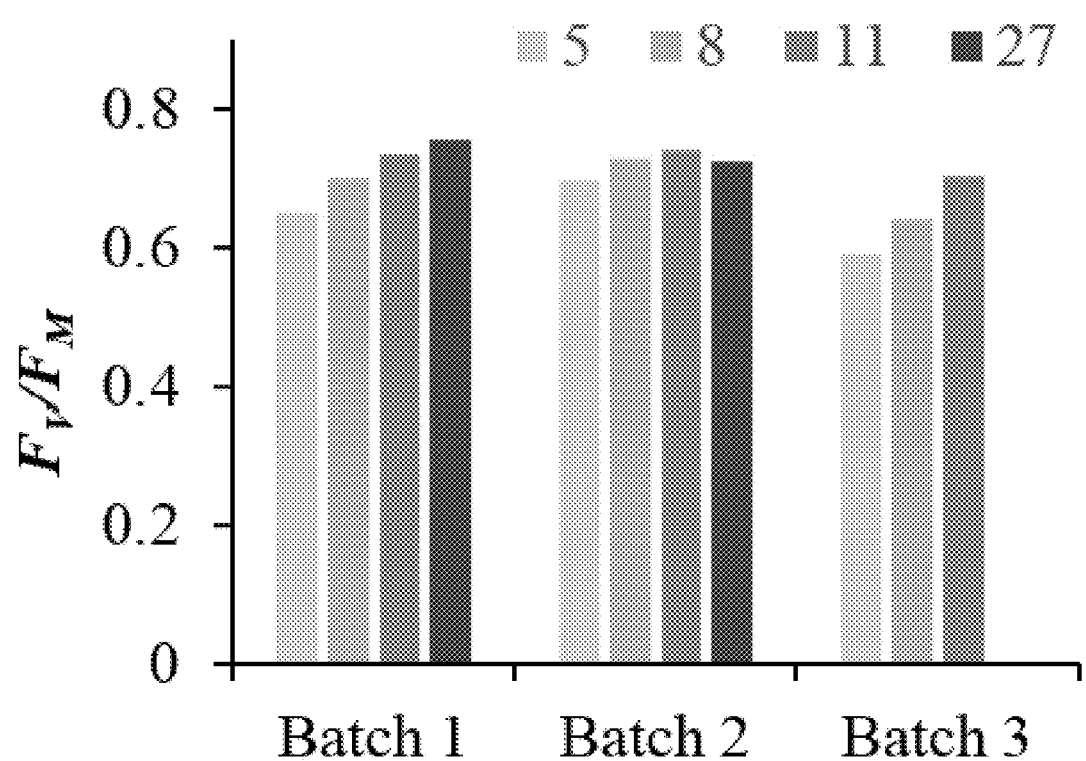
Figure 14F:
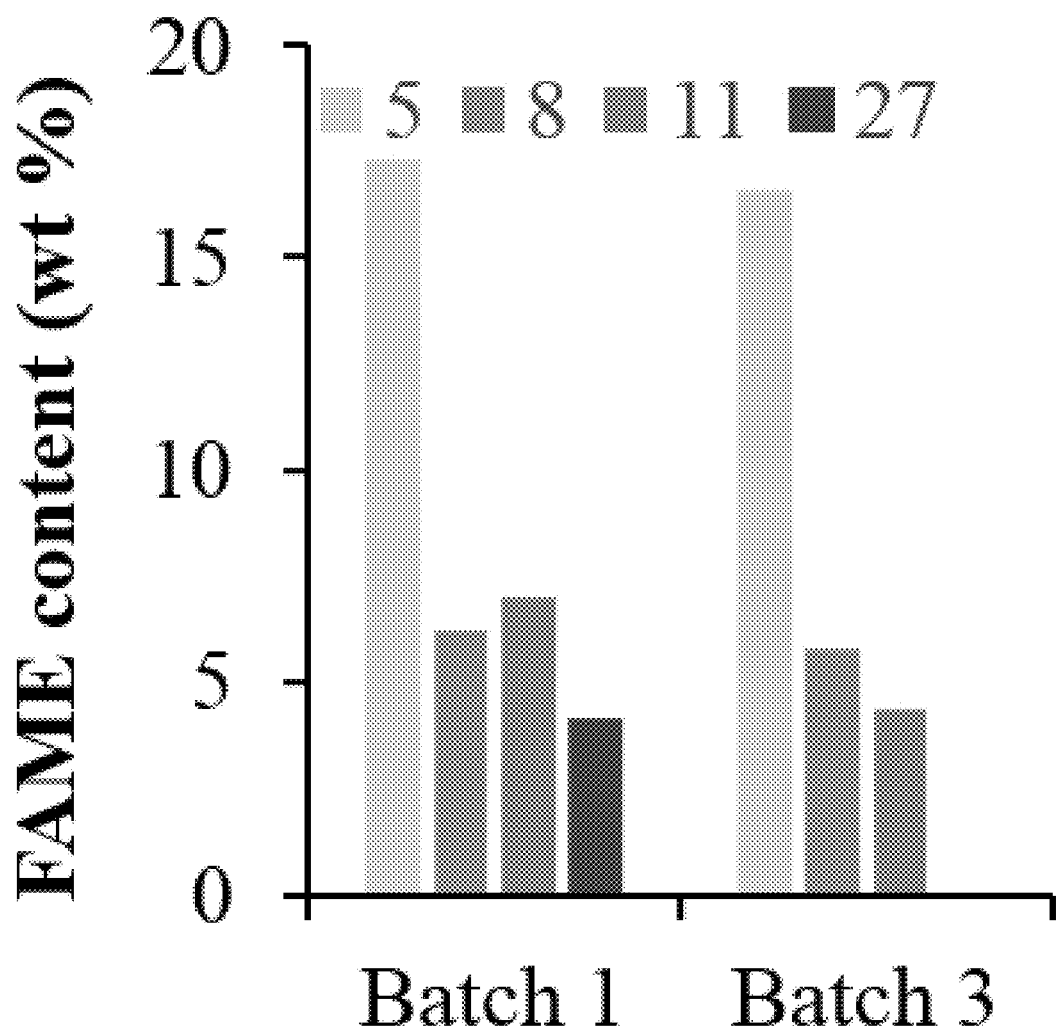

FIG. 14A depicts biomass productivity of SLA-04 on media N input conditions. The results show when the media N input increased, there was an increase in biomass productivity (FIG. 14A). Since chlorophyll is the nitrogenous compound among others, as media N concentrations increases, there is an increase in chlorophyll content (FIG. 14C). Hence, when considering chlorophyll concentration (FIG. 14C), the biomass productivity of SLA-04 per chlorophyll content was observed to decrease along with an increase in media N input (FIG. 14B). Without wishing to be bound by theory, it is believed this is due to the light limitation to chlorophyll present in cells being present at greater pond depths that results in a decrease in biomass productivity relative to chlorophyll content. As the N input increases, there is an abundant availability of nitrogen source and cultures tend to accumulation nitrogenous compounds (e.g., chlorophyll and related proteins). This results in increased nitrogen content in biomass (range: 3.5-7.2%) (FIG. 14D). $F_v/F_m$ factor, which represents PSII maximum quantum yield at dark adapted state for cultures, is shown in FIG. 14B. Among other nutrients, nitrogen stress for culture (that damages PSII) decreases $F_v/F_m$. The results show $F_v/F_m$ is increased in increase in order with media N content (5-27 mg/L). Even though $F_v/F_m$ of cultures fed with low N (5-8 mg/L) had low $F_v/F_m$, it did not show a significant effect on biomass growth and productivity (FIG. 14A). Nitrogen stress condition in microalgae can inhibit further cell reproduction and induce lipid synthesis as an energy storage process. Fatty acid methyl esters (FAME) data indicate that the cultures fed at N input 5 mg/L had four folds higher FAME content (16%) than cultures fed at N input 27 mg/L (4.1%) (FIG. 14F). Low $F_v/F_m$ is the indicator of stress condition for cultures fed with low (5 mg/L) N input prone to induce lipid biosynthesis and thereby shown increased FAME content. Table 4 depicts the biochemical composition of SLA-04 fed at different N input. The results confirm one can modulate the biochemical composition of the microalgae by regulating media N input.

TABLE 4

Biochemical composition of SLA-04 grown under different N input environment

| Sample Name | Carbohydrate (%) | Ash (%) | Protein (%) | Fame (%) | Moisture (%) | Total |
|---|---|---|---|---|---|---|
| 5 mg/L N-Batch1 | 33.15 | 6.47 | 22.724 | 17.34 | 6.8 | 86.48 |
| 8 mg/L N-Batch1 | 30.49 | 6.70 | 35.88 | 6.20 | 7.58 | 86.85 |
| 11 mg/L N-Batch1 | 15.00 | 6.30 | 42.458 | 7.00 | 7.93 | 78.69 |
| 27 mg/L N-Batch1 | 13.88 | 8.50 | 43.056 | 4.00 | 8.03 | 77.47 |
| 5 mg/L N-Batch3 | 36.31 | 5.75 | 22.724 | 16.56 | 6.39 | 87.73 |
| 8 mg/L N-Batch3 | 27.91 | 5.20 | 33.488 | 6.00 | 7.73 | 80.33 |
| 11 mg/L N-Batch3 | 13.40 | 6.50 | 43.056 | 4.00 | 8.2 | 75.15 |

Example 7: Nitrogen Utilization by SLA-04 and Effect of N Input on SLA-04 Biochemical Composition—Outdoor Experiments at 1100 L Scale Based on the above experiment, it is important to start cultures with the same chlorophyll concentration to evaluate the effect of media N input on biomass production. The initial chlorophyll concentration was adjusted to a similar concentration by appropriate dilution of inoculum for all N input culture conditions. The experiments were conducted in big raceway ponds (1100 L) with working volume of 500 L and at ~5 inches' depth. Initial media N input was adjusted to a range of 5-15 mg/L using sodium nitrate as a nitrogen source.

Figure 15A:
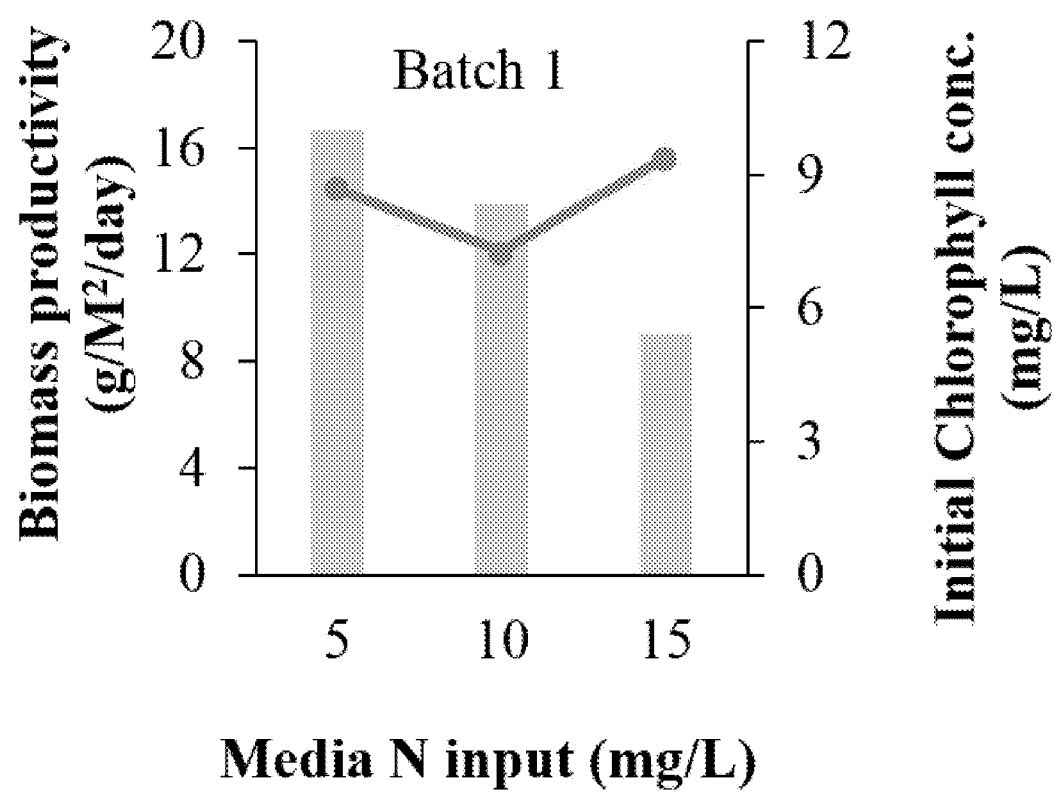
FIGS. 15A-15B: Effect of media N input on SLA-04 cultures cultivated in 1100 L reactors.
Figure 15B:
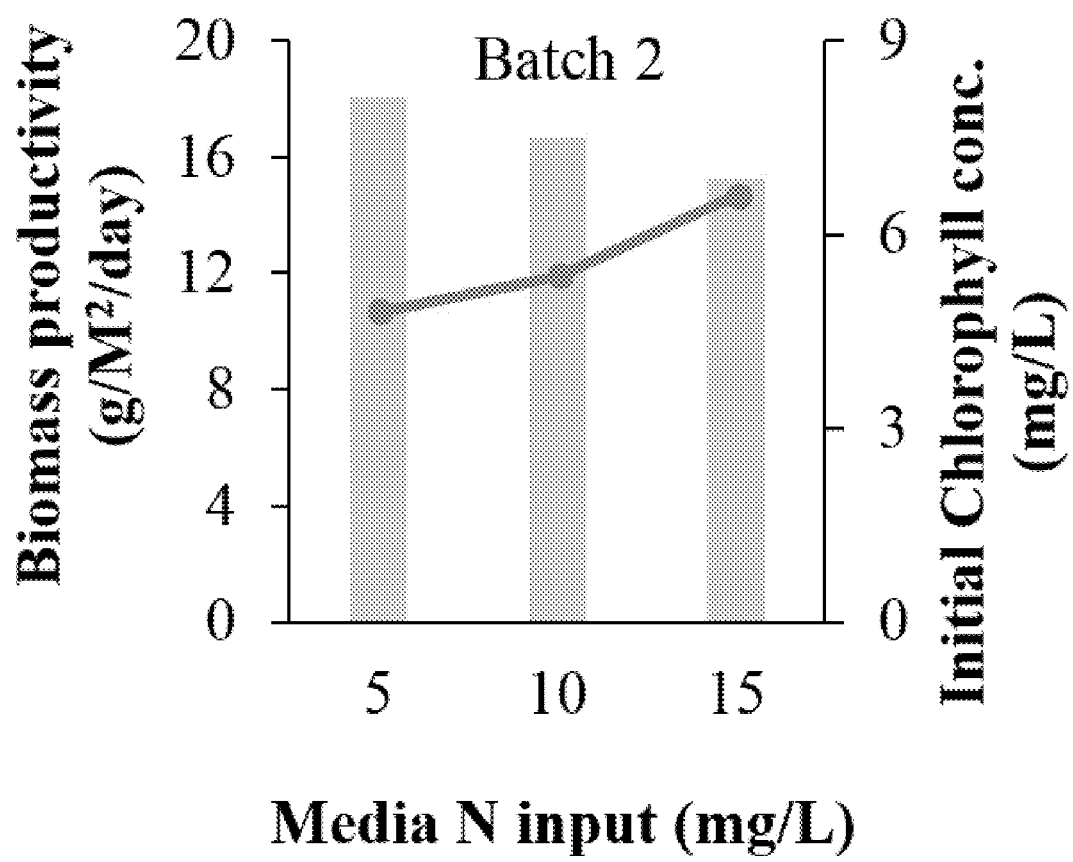

Cultures fed with N concentration 5 mg/L showed higher biomass productivity than cultures fed with N concentration 10 and 15 mg/L (FIGS. 15A-15B). The results indicate the biomass productivity increases as the N input decreases in media because of two factors: i) high cell concentration at N limitation conditions provide more cellular machinery for carbon fixation, and ii) as the growth proceeds, the chlorophyll content of cultures supplemented with high N availability increases, prone to light limitation to deeper layers when compared with cultures supplemented with low N input.

The presence of high media alkalinity also decreases the N uptake by SLA-04 (FIG. 5D). Overall, these results show that by adjusting media alkalinity and N supply, biomass with low N-content (~3%) can be produced. Cultures grown outdoors (FIGS. 8A, 9) also had an N-content of ~3%. Most other microalgae have an N content of 4-8%.

Example 8: Optimization of Micro-Nutrient Utilization by SLA-04

Effect of Ca and Mg on Growth of SLA-04

Figure 12:
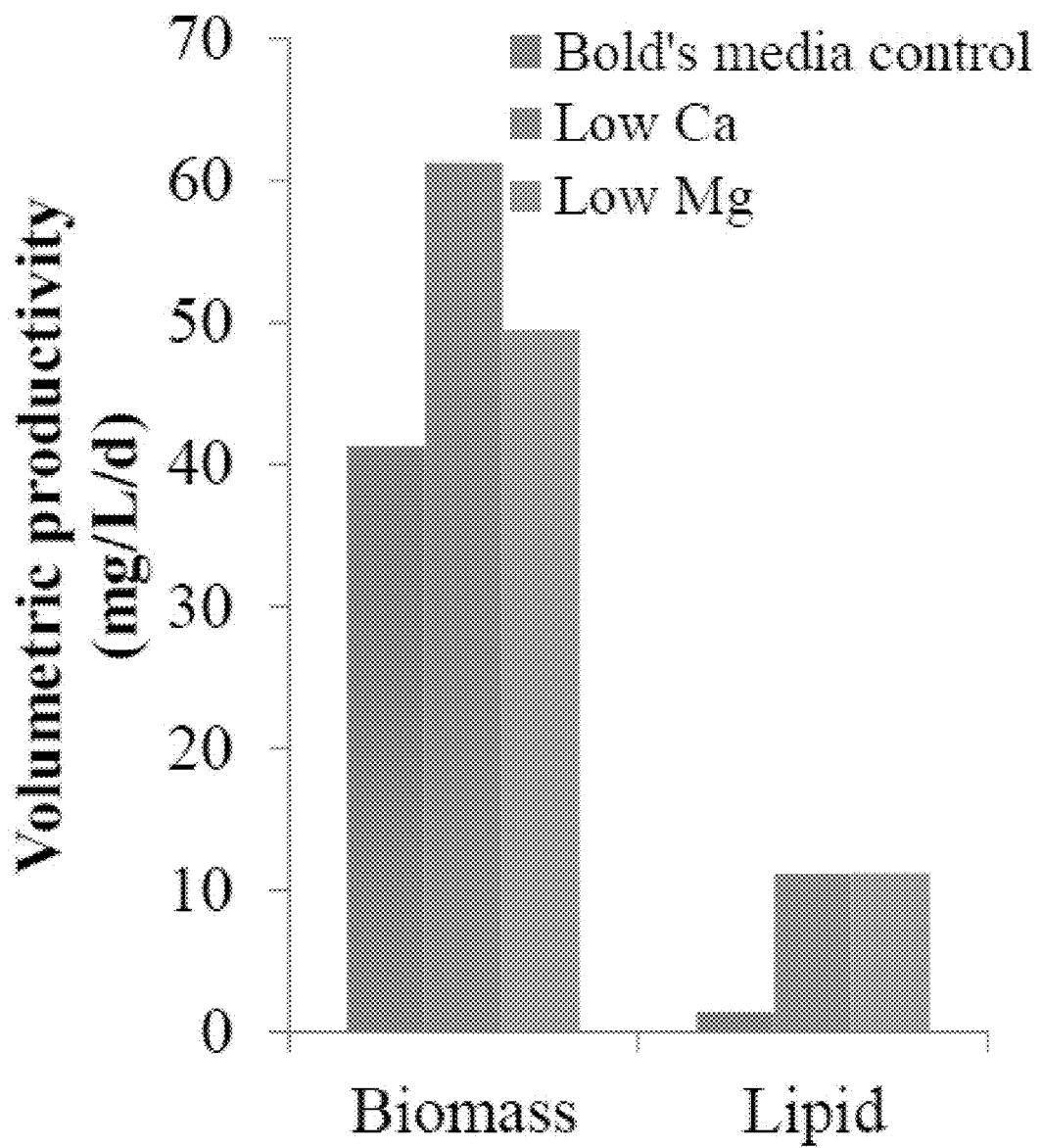
FIG. 12: SLA-04 productivities in high and low Ca/Mg media.

It was observed that biomass and lipid productivities can be improved (up to 33%) through use of low concentrations of Ca and Mg (<1.5 mg-Ca/L and <0.5 mg-Mg/L) (FIG. 12). Most microalgae growth media recipes have much higher Ca and Mg. For example, Ca and Mg concentrations in Bold's medium are nearly 7 mg/L. This finding—that under alkaline conditions, it is possible to achieve higher biomass productivities and lipid accumulation at significantly lower levels of Ca and Mg compared to traditional Bold's medium—has very favorable economic implications in large-scale outdoor algae cultivations.

Effect of Salinity (NaCl) on Growth of SIA-04

Lowering fresh water requirements is important for sustainable microalgae cultivation. Saltwater is a more sustainable water source than fresh water. For instance, seawater is inexpensively accessible in coastal areas of the southeast US (e.g. Florida and other Gulf states) and brackish water is abundant in southwest US (e.g. Arizona, New Mexico, Texas). These locations also have the most appropriate weather for microalgae cultivation. Str. SLA-04 can thrive in high salinity media as it was isolated from saline-alkaline lake (Soap Lake, State of Washington).

Growth of the isolated strain *C. sorokiniana* str. SLA-04 was examined in a BG-11 medium with nitrate content 40 mg/L and similar salinity to seawater (30 g/L). An appropriate proportion (2:3) of $NaHCO_3^-$ and $Na_2CO_3^{2-}$ were added as an inorganic carbon source to get a final $HCO_3^-$ concentration (30 mM) and initial pH 10.1. The experiment was performed in 3 L reactors under 800 μmoles/m²/s light illumination and light-dark cycles of 10 h/14 h.

Figure 16A:
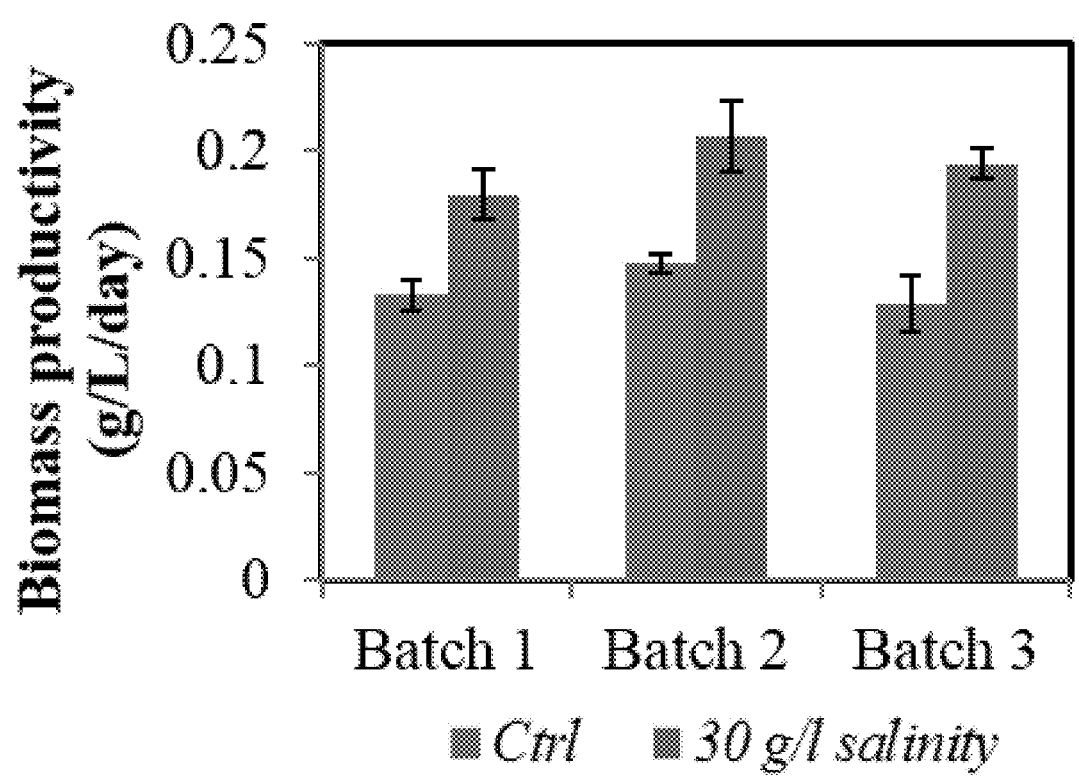
FIGS. 16A-16B: Biomass productivity (FIG. 16A), and maximum quantum yield of cultures grown with and without salinity conditions (FIG. 16B).
Figure 16B:
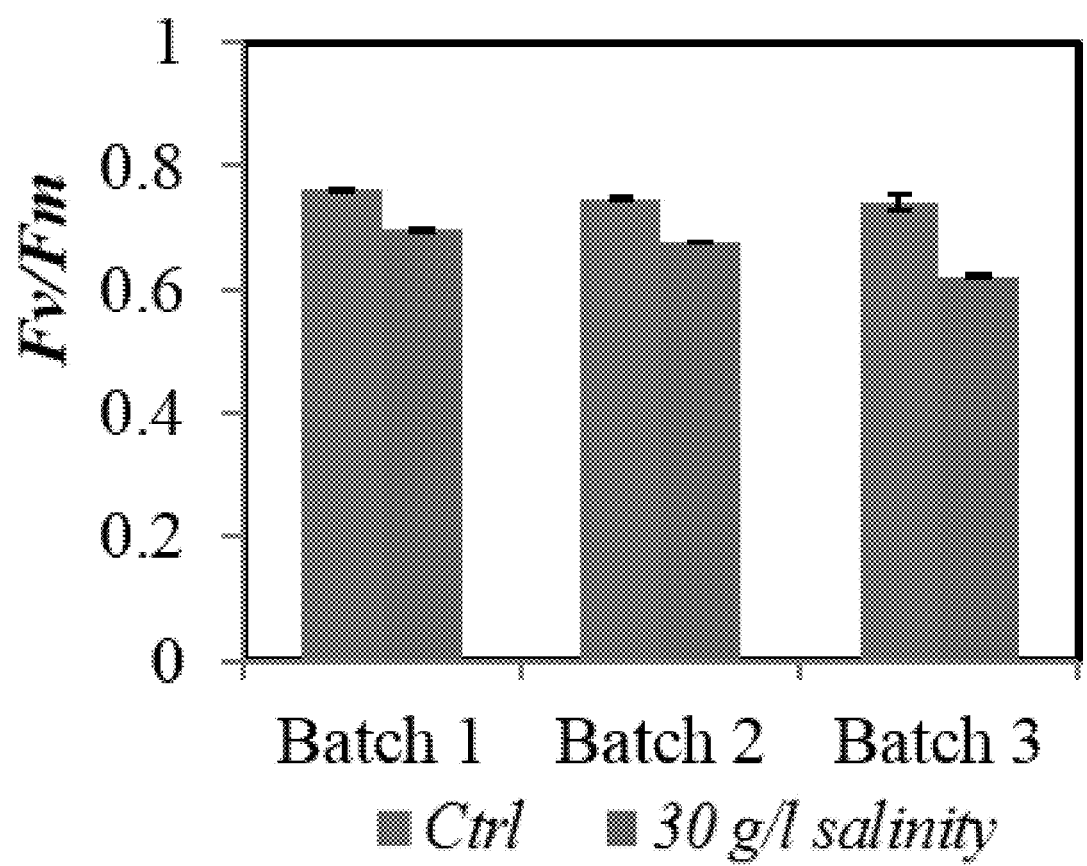

Interestingly, the results show improvement of biomass productivity of SLA-04 with medium containing high salinity (FIG. 16A). Such improvement can be assigned to three factors: 1) increased availability of sodium ions, which are required for pH homeostasis of alkaliphilic *C. sorokiniana* str. SLA-04; 2) the Henry constant for dissolution of $CO_2$ in water increases by increase in salinity, which improves carbon capturing and inorganic carbon availability for salty cultures; and 3) there is a lower pigmentation of microalgae cells grown in saltwater than fresh water, which therefore increase light availability. $F_v/F_m$ factor, which represents PSII maximum quantum yield at dark adapted state for indoor cultures, is shown in FIG. 16B. Any environmental or nutritional stress for culture (that damages PSII) decreases $F_v/F_m$. The results show there is no significant difference in $F_v/F_m$ between cultures grown with salinity and cultures grown without salinity.

The outdoor experiment was conducted with the same media conditions as the indoor experiment to examine the application of this method for more cost-efficient and manageable open ponds. To evaluate the effect of salt concentration, two different salt concentrations (18 g/L and 30 g/L) were used. The experiments were conducted in open raceway ponds (30 L) with working volume of 18 L, and were performed in sequential batches that each lasted 2 days.

Figure 17A:
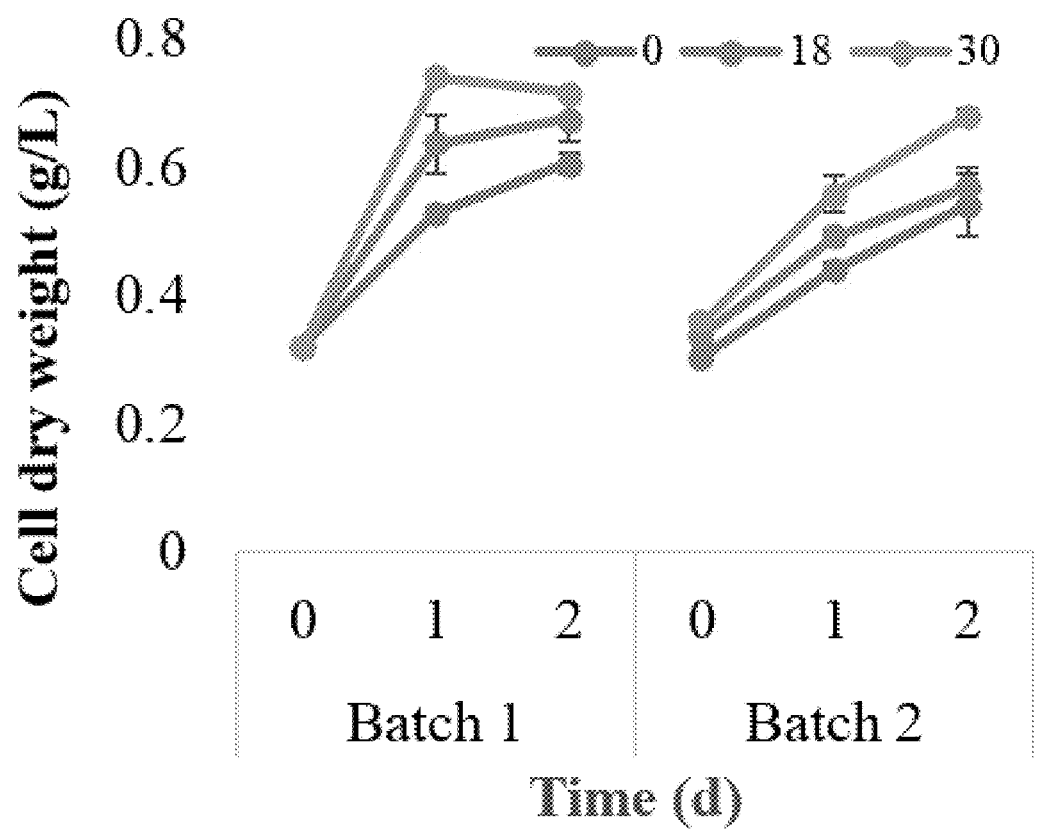
FIGS. 17A-17D: Cell dry weight (FIG. 17A), biomass productivity (FIG. 17B), chlorophyll content (FIG. 17C), and chlorophyll a/b ratio of cultures grown with salinity (0-30 g/L) (FIG. 17D).
Figure 17B:
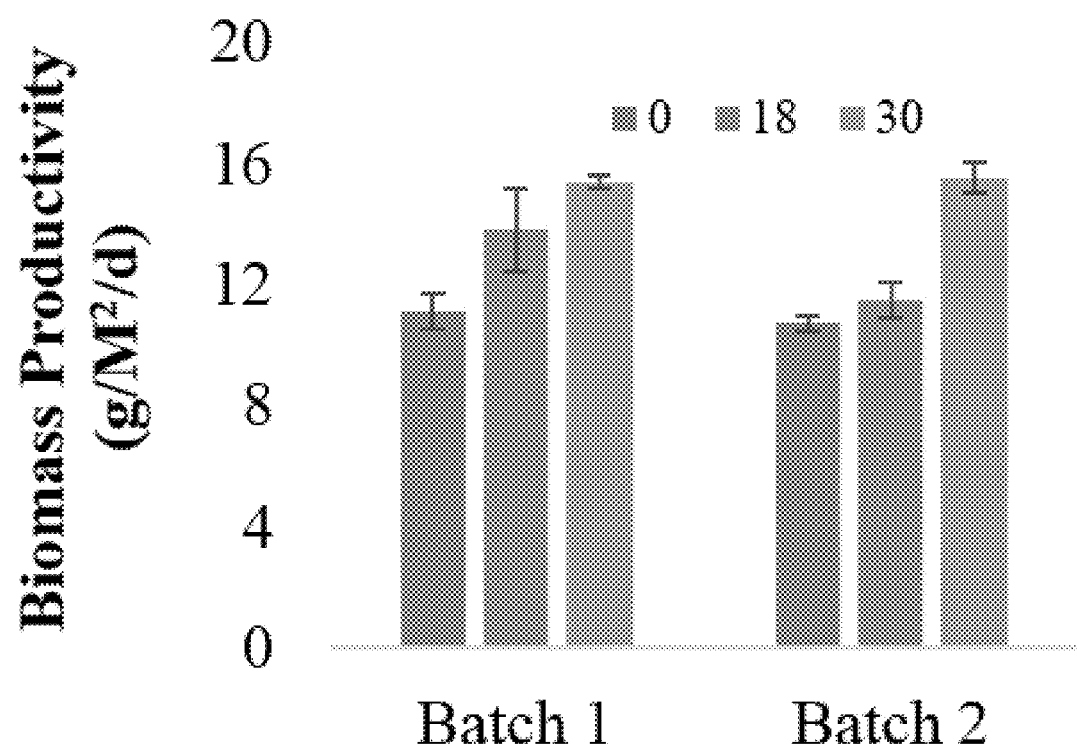
Figure 17C:
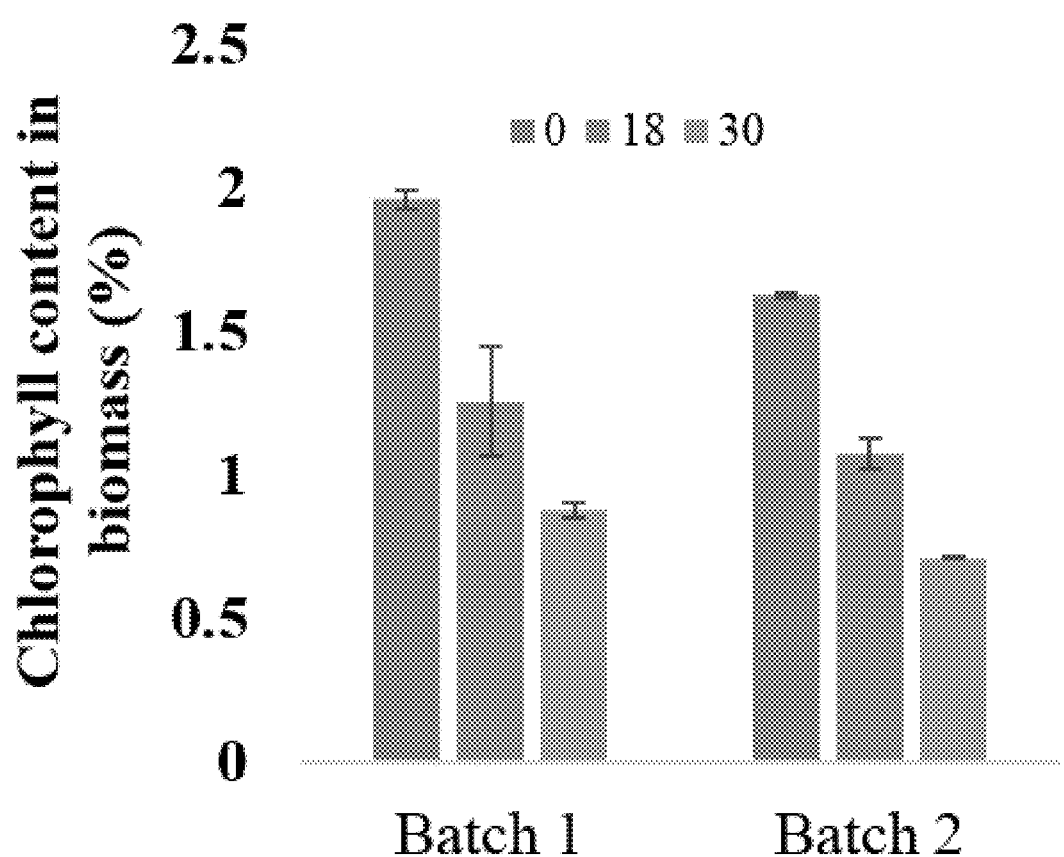
Figure 17D:
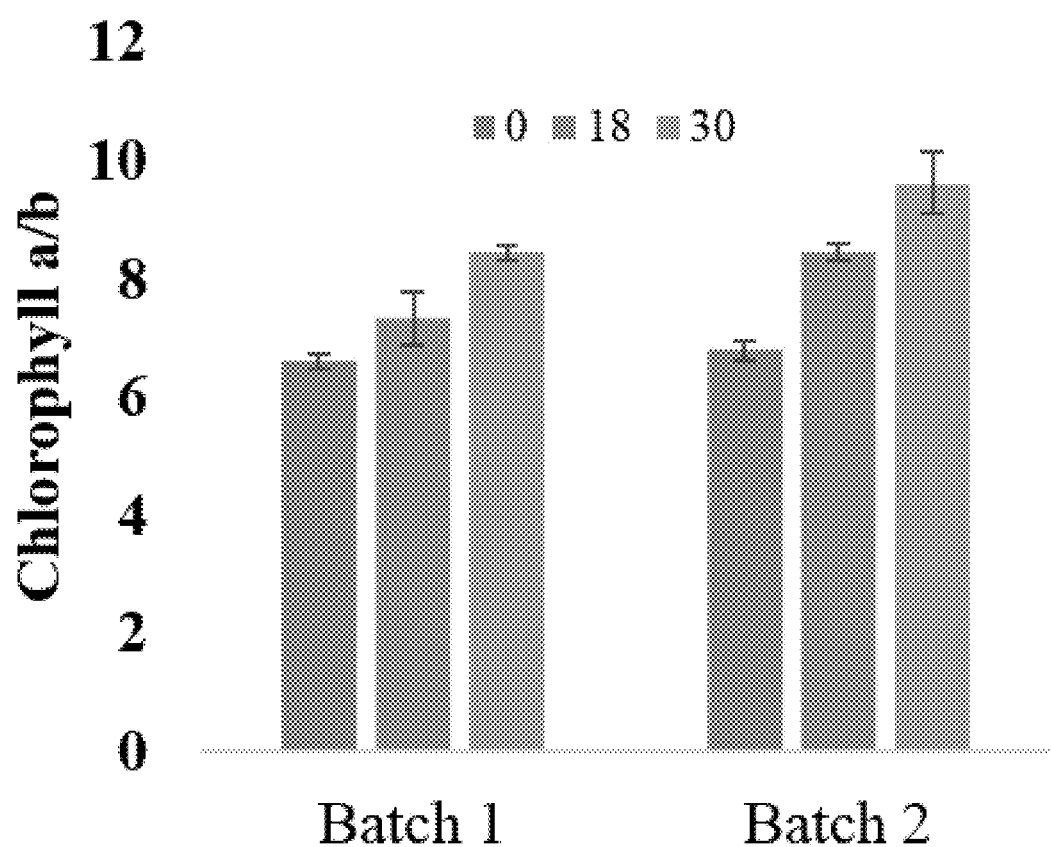

FIG. 17A and FIG. 17B illustrate the growth pattern and biomass productivity of SLA-04. The results indicate biomass productivity is increased on the order of salt concentration increases in the medium (FIG. 17A). Chlorophyll a is the pigment that interacts directly in the light requiring reactions of photosynthesis, whereas chlorophyll b is an accessory pigment and acts indirectly in photosynthesis by transferring light it absorbs to chlorophyll a. Excessive accumulation of chlorophyll b limits the light penetration in to deeper layers. Low light availability further decrease photosynthetic activity and increase respiration rates, and is thereby attributed to low productivity. The lower chlorophyll concentration and higher chlorophyll a/b ratio of the cultures is the indication of efficient light penetration and photosynthetic efficiency for the cultures with high salinity (FIGS. 17C-17D). The Henry constant for dissolution of $CO_2$ in water increases by the increase in salinity, which results in higher atmospheric carbon capture under salinity conditions (Table 5). Overall, these results are in accordance with indoor experiments and indicate that saltwater can be used as an inexpensive water source to enhance the biomass productivity and carbon capturing.

TABLE 5

Carbon balance of SLA-04 grown under different salinity conditions

|  | Assimilated organic carbon (mM) | | | Inorganic carbon depletion (mM) | | | Atmospheric carbon captured (mM) | | |
| --- | --- | --- | --- | --- | --- | --- | --- | --- | --- |
|  | 0 g/L | 18 g/L | 30 g/L | 0 g/L | 18 g/L | 30 g/L | 0 g/L | 18 g/L | 30 g/L |
| Batch 1 | 5.3 | 6.7 | 7.4 | 0.3 | 0.5 | 0.4 | 5 | 6.1 | 7 |
| Batch 2 | 4.5 | 4.3 | 6.1 | 0.6 | 0.1 | 0.3 | 3.9 | 4.2 | 5.8 |

Effect of Salinity on Phycocyanin Production

Phycocyanin is a light-harvesting pigment and nitrogen-storing protein found in the prokaryotic cyanobacteria species, as well as in eukaryotic microalgae. Phycocyanin is widely used in pharmaceuticals and blue pigments. It is used as a natural dye for foods and cosmetics. *Chlorella sorokiniana* is one of the highest natural sources of phycocyanin and chlorophyll. Hence, the strain *C. sorokiniana* str. SLA-04 has the ability to produce phycocyanin. Environmental stresses such as light intensity, culture concentration, salinity, pH, and nitrogen availability can influence phycocyanin production in microalgae. In this example, the effect of salt concentration, inoculum concentration, and nitrogen content on phycocyanin production of *C. sorokiniana* str. SLA-04 was evaluated.

Culture conditions: since phycocyanin is the nitrogen storage compound, when compared to the above-described outdoor experiment, the medium nitrate concentration was increased from 40 mg/L to 150 mg/L to provide nitrogen abundant environment. Also, inoculum concentration was increased from 0.32 to 0.75 g/L.

Figure 18A:
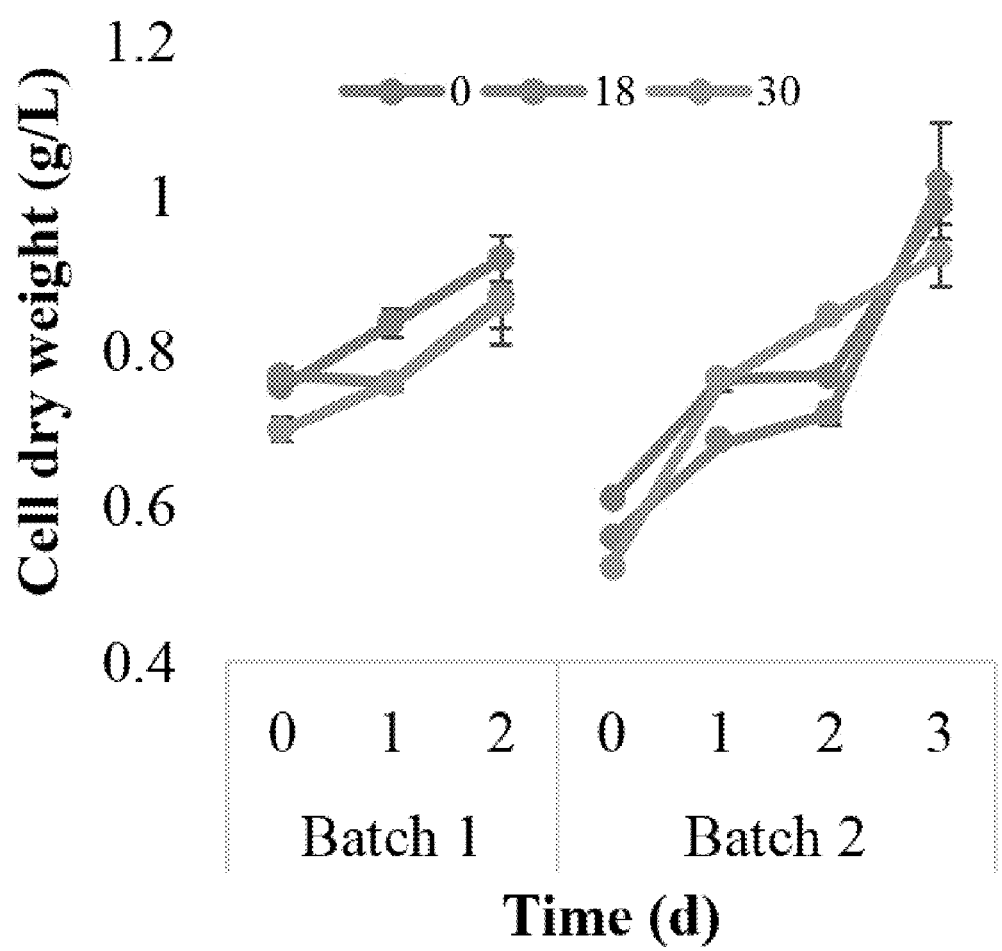
FIGS. 18A-18E: Cell dry weight (FIG. 18A), biomass productivity (FIG. 18B), phycocyanin content (FIG. 18C), chlorophyll content (FIG. 18D), and chlorophyll a/b ratio of cultures grown with salinity (0-30 g/L) (FIG. 18E).
Figure 18B:
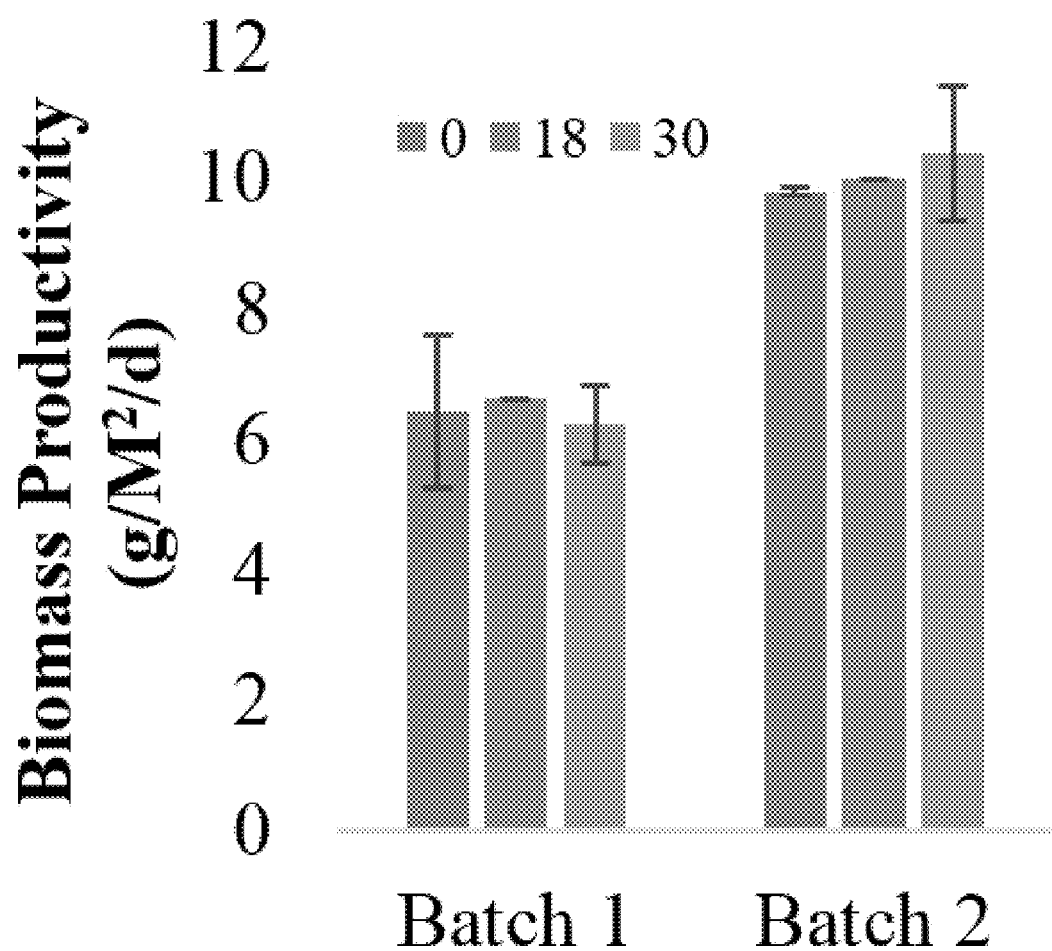
Figure 18C:
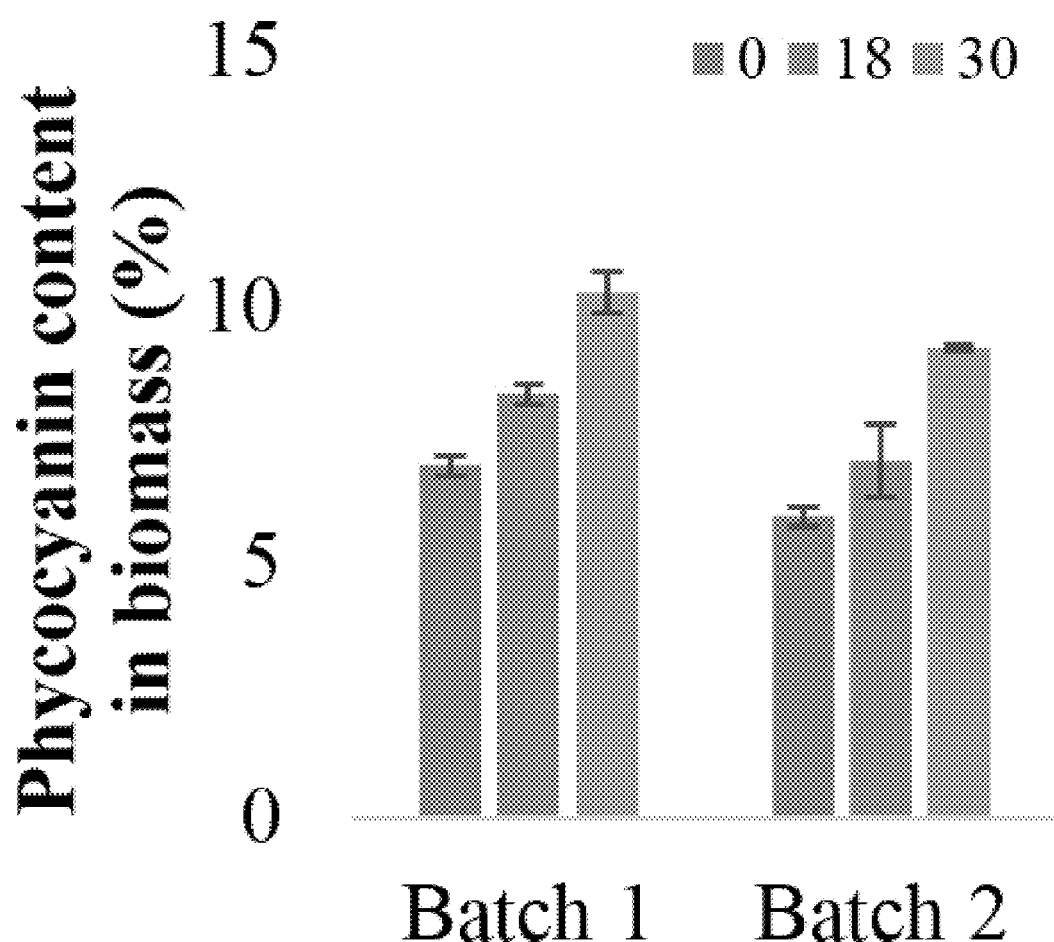
Figure 18D:
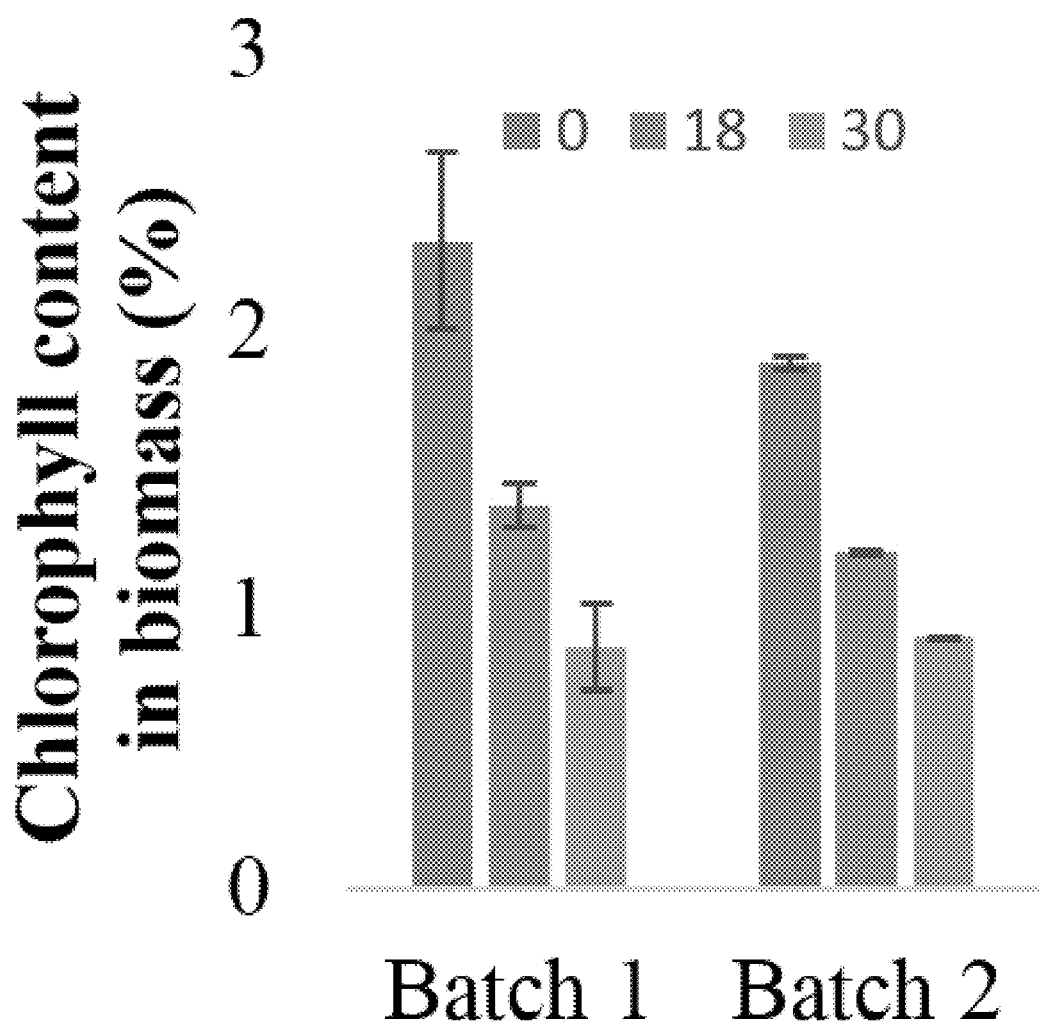

FIGS. 18A-8B depict growth and average biomass productivity of the SLA-04 under the culture conditions. In contrast to the above-described experiments, the results show there is no significant difference in biomass growth and productivity between cultures grown with and without salinity. Without wishing to be bound by theory, it is believed this is due to the high pigmentation noticed in saline cultures (FIGS. 18C-18D). A comparative analysis between batch 1 and batch 2 cultures indicated that cultures started with low inoculum concentration showed higher biomass productivity. This is attributed to better light penetration.

Figure 18E:
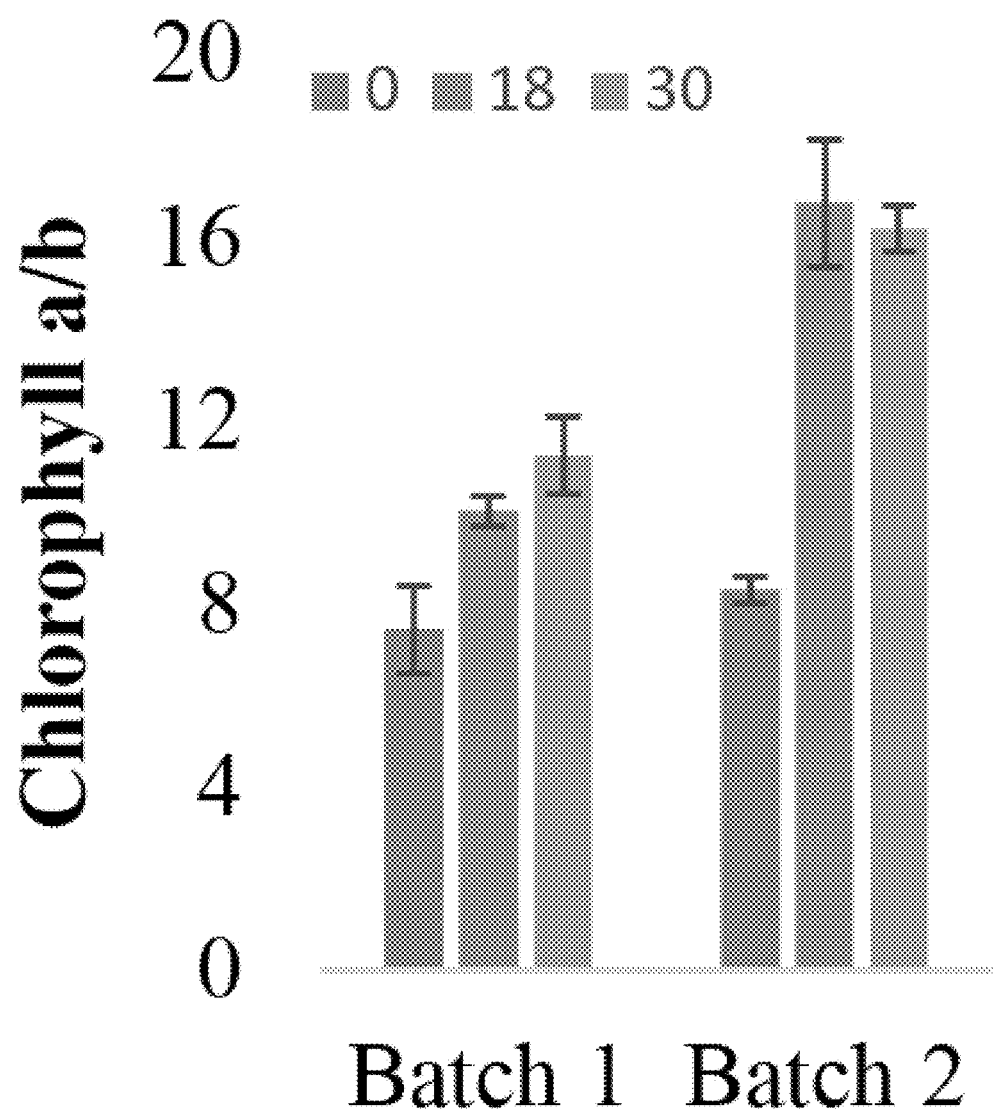

FIGS. 18C-18D show pigmentation (phycocyanin and chlorophyll) of SLA-04 under culture conditions. The results show salt stress increased the phycocyanin content in biomass. As the salt concentration increases, phycocyanin content in biomass was observed to be increased in order (FIG. 18C). Like the above-described experiments, the results revealed a decrease in total chlorophyll content and an increase in chlorophyll a/b ratio with respect to salt concentration in the medium (FIGS. 18D-18E).

Certain embodiments of the methods and systems disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method for culturing algae, the method comprising:
   culturing alkaliphilic algae in an open pond medium having a pH above 9.5, sufficient to allow increased fixation of atmospheric $CO_2$ into the open pond medium; and
   incorporating into the open pond medium an inorganic carbon buffer, wherein the inorganic carbon buffer comprises $HCO_3^-$ present at a concentration ranging from 4.5 mM to 60 mM and the open pond medium has a salinity in the range of from about 10 g/L to about 30 g/L and an alkalinity of up to about 1 M;
   wherein the open pond medium is free of any concentrated supply of $CO_2$, and no concentrated source of $CO_2$ is used to supply carbon for culturing the alkaliphilic algae.

2. The method of claim 1, wherein the inorganic carbon buffer comprises either a $NaHCO_3/Na_2CO_3$ mixture or a $KHCO_3/K_2CO_3$ mixture.

3. The method of claim 2, wherein the $NaHCO_3/Na_2CO_3$ mixture or the $KHCO_3/K_2CO_3$ mixture is incorporated into the open pond medium at a concentration ranging from about 7 mM to about 60 mM.

4. The method of claim 1, wherein the pH of the open pond medium is at least about 9.9.

5. The method of claim 1, further comprising incorporating glucose or other sugars or carboxylic acids into the open pond medium.

6. The method of claim 1, wherein the algae comprise a *Chlorella* sp., *Dunaliella* sp., *Synechocystic* sp., *Cyanothece* sp., *Microcoleus* sp., *Euhalothece* sp., or *Spirulina* sp. strain.

7. The method of claim 1, further comprising incorporating Ca and/or Mg into the open pond medium at a concentration of less than 7 mg/L.

8. The method of claim 7, wherein the Ca is incorporated into the open pond medium at a concentration of less than 1.5 mg Ca/L.

9. The method of claim 7, wherein the Mg is incorporated into the open pond medium at a concentration of less than 0.5 mg Mg/L.

10. The method of claim 1, further comprising circulating the algae within the open pond medium.

11. The method of claim 1, further comprising harvesting biomass from the cultured algae and recovering remnant media.

12. The method of claim 11, further comprising recycling the remnant media in a second open pond medium.

13. The method of claim 11, further comprising converting the harvested biomass to one or more fuels.

14. The method of claim 13, wherein the converting comprises hydrothermal liquefaction to produce biocrude having a N content of less than 4%.

15. The method of claim 1, further comprising regulating nitrogen input in the open pond medium, in a range from about 5 mg/L to about 27 mg/L, so as to modulate the biochemical composition of the algae.

16. The method of claim 1, wherein the pH of the open pond medium is greater than 10.0.

17. The method of claim 1, wherein the alkaliphilic algae comprise eukaryotic microalgae.

18. A method for culturing algae, the method comprising:
   culturing alkaliphilic algae in an open pond medium having a pH above 9.5, sufficient to allow increased fixation of atmospheric $CO_2$ into the open pond medium; and
   incorporating into the open pond medium an inorganic carbon buffer, wherein the inorganic carbon buffer comprises $HCO_3^-$ present at a concentration ranging from 4.5 mM to 60 mM and the open pond medium has a salinity in the range of from about 10 g/L to about 30 g/L and an alkalinity of up to about 1 M;
   wherein the open pond medium is free of any concentrated supply of $CO_2$, and no concentrated source of $CO_2$ is used to supply carbon for culturing the alkaliphilic algae, the method using atmospheric $CO_2$ alone.

19. A method for culturing an alkaliphilic algal strain, the method comprising:
culturing the alkaliphilic algal strain, the algal strain comprising microalgae or cyanobacteria, in an open pond medium having a pH above 9.5, sufficient to allow increased fixation of atmospheric $CO_2$ into the open pond medium, and a salinity in the range of from about 10 g/L to about 30 g/L, free of any concentrated supply of $CO_2$, and no concentrated source of $CO_2$ is used to supply carbon for culturing the alkaliphilic algal strain;
incorporating into the open pond medium an inorganic carbon buffer at a total alkalinity ranging from about 3 mM to about 1 M;
regulating nitrogen input in the open pond medium, in a range from about 5 mg/L to about 25 mg/L; and
recovering the cultured algal strain.

* * * * *